(12) United States Patent
De Beni et al.

(10) Patent No.: US 11,510,656 B2
(45) Date of Patent: Nov. 29, 2022

(54) ULTRASOUND IMAGING METHOD AND ULTRASOUND IMAGING SYSTEM THEREFOR

(71) Applicants:Esaote S.p.A., Genoa (IT); MedCom GmbH, Darstadt (DE)

(72) Inventors: Stefano De Beni, Genoa (IT); Antonella De Rosa, Genoa (IT); Velizar Kolev, Darmstadt (DE); Georgios Sakas, Darmstadt (DE)

( * ) Notice: Subject to any disclaimer, the term of this patent is extended or adjusted under 35 U.S.C. 154(b) by 356 days.

(21) Appl. No.: 16/774,879

(22) Filed: Jan. 28, 2020

(65) Prior Publication Data

US 2020/0237347 A1 Jul. 30, 2020

(30) Foreign Application Priority Data

Jan. 30, 2019 (EP) .................................. 19154388

(51) Int. Cl.
*A61B 8/00* (2006.01)
*A61B 8/08* (2006.01)
(Continued)

(52) U.S. Cl.
CPC ............ *A61B 8/5238* (2013.01); *A61B 8/463* (2013.01); *A61B 8/466* (2013.01); *B29C 64/386* (2017.08); *B33Y 50/00* (2014.12); *G06T 17/00* (2013.01); *G16H 15/00* (2018.01); *G16H 30/20* (2018.01); *G16H 30/40* (2018.01); *G16H 50/50* (2018.01); *A61B 8/0825* (2013.01); *A61B 2090/367* (2016.02); *G06T 2210/41* (2013.01)

(58) Field of Classification Search
None
See application file for complete search history.

(56) References Cited

U.S. PATENT DOCUMENTS

| 2009/0209851 | A1* | 8/2009 | Blau | A61B 90/37 |
| | | | | 600/426 |
| 2017/0258526 | A1* | 9/2017 | Lang | A61B 17/1742 |
| 2017/0340389 | A1* | 11/2017 | Otto | A61B 5/1075 |

FOREIGN PATENT DOCUMENTS

EP 3400878 11/2018

OTHER PUBLICATIONS

Blackall, JM: Respiratory Motion in Image-Guided Interventions in the Liver, London (Sep. 2002) Abstract; Sections 1-5.
(Continued)

*Primary Examiner* — Joel F Brutus
(74) *Attorney, Agent, or Firm* — Themis Law

(57) ABSTRACT

An ultrasound imaging method includes providing a digital representation of the shape of a surface or boundary of an anatomic region or organ; acquiring an ultrasound image by ultrasound scanning the anatomic region or organ; and combining the digital representation of the shape of the surface or boundary of the anatomic region or organ by registering the digital representation of the shape of the surface or boundary and the ultrasound image as a function of the difference in position of selected reference points on the digital representation of the surface or boundary and on the ultrasound image, the position of the reference points on the ultrasound image being determined by tracking the probe position at the reference points at the anatomic region or organ of a real body and in a spatial reference system, in which the anatomic region or the organ of the real body is placed.

16 Claims, 19 Drawing Sheets

(51) Int. Cl.
| | |
|---|---|
| *B33Y 50/00* | (2015.01) |
| *B29C 64/386* | (2017.01) |
| *G16H 50/50* | (2018.01) |
| *G16H 15/00* | (2018.01) |
| *G16H 30/20* | (2018.01) |
| *G16H 30/40* | (2018.01) |
| *G06T 17/00* | (2006.01) |
| *A61B 90/00* | (2016.01) |

(56) References Cited

OTHER PUBLICATIONS

Mauri, G. et al.:Real-Time US-18FDG-PET/CT Image Fusion for Guidance of Thermal Ablation of 18-FDG-PET-Positive Liver Metastases: The Added Value of Contrast Enhancement, Cardiovascular and Interventional Radiology, Springer Verlag, Inc., New York, NY, vol. 42, No. 1 (Oct. 4, 2018), pp. 60-68 Abstract; figs. 1-2; Section "Methods".

* cited by examiner

ULTRASOUND IMAGING METHOD AND ULTRASOUND IMAGING SYSTEM THEREFOR

FIELD OF THE INVENTION

The present invention relates to an ultrasound imaging method and system. More particularly, the present invention relates to an ultrasound method and related system capable of combining morphological information on the shape of a surface or a boundary of an anatomic region or of an organ.

BACKGROUND OF THE INVENTION

Imaging methods that provide the combination of ultrasound images of the internal structure of a target with the image or the representation of the shape of the external surface of the target are known.

A particular application of this generic technique is related to combining ultrasound images of the internal morphology of the tissues at certain anatomic regions of a body of a patient or of certain selected organs with a representation of the external surface of the anatomic regions of the body of the patient or of the selected organs.

Examples of these known techniques are disclosed in document EP3400878 or in document WO2012112907.

EP3400878 discloses a method for postural independent location of targets in diagnostic imagines acquired by multimodal acquisitions comprising the steps of:

generating a transition of a digital image of the inside of a target region from a first to a second position of the target region by correlating the position of markers placed on the external surface of the target region in the digital image of the inside of the target region and in a digital representation of the surface of the target region acquired by optical scanning the surface; and at a later time, registering the diagnostic image of the inside of the target region which has been transitioned into the second position with a diagnostic image of the same target region acquired with the target region in the second position by matching a second representation of the external surface of the target body in the second position without markers with the diagnostic image of the inside of the target region which has been transitioned into the second position.

This method is applied for postural independent location of targets in diagnostic images acquired by multimodal acquisitions, this method allowing to compensate for the deformation to which soft tissues are subject by changing posture of the patient and particularly in the conditions in which such deformations have an effect on the external visible shape of parts of the body or of the object.

WO2012112907 discloses a method for registering an optically scanned surface image with a volumetric image, comprising the steps of:

obtaining a volumetric image created at a first time;

obtaining a surface optically scanned image created at a second time;

identifying spatial locations of fiducial markers from the volumetric image and the surface image; and using fiducial locations to perform rigid body registration between the volumetric image and the surface image.

In the above disclosed methods an optical scan of the anatomic region is carried out for generating the representation of the external surface of the anatomic region. However, this step is possible if the method is applied to anatomic regions which have an air/tissue boundary, such as the specific examples of the breast to which both cited documents are directed. The method cannot be applied to internal anatomic regions or organs which are also formed by soft tissues and have a patient specific shape which is also subject to deformation due to postural changes of the patient or to the pressure exercised by the ultrasound probe during the ultrasound imaging scan.

The method according to the state of the art comprises the steps of:

providing a digital representation of the shape of the surface or boundary of an anatomic region or of an organ;

acquiring an ultrasound image by ultrasound scanning the anatomic region or the organ;

combining the digital representation of the shape of the surface or boundary of the anatomic region or of the organ by:

registering the digital representation of the shape of the surface or boundary and the ultrasound image as a function of the difference in position of selected reference points un the digital representation of the surface or boundary and on the ultrasound image, the position of the reference points on the ultrasound image being determined by tracking the probe position at the reference points at the anatomic region or organ of a real body and in a spatial reference system in which the anatomic region or the organ of the real body is placed.

The digital representation of the shape of the surface or of the boundary of an anatomic region or of an organ has to be carried out by optically scanning the anatomic region or the organ or by drawing it. This step has to be carried out for every different patient. As a consequence, obtaining such combined multimodal images needs longer time since the step of acquiring the optical scan or for extracting the surface or boundary of an organ or for drawing such surface or boundary has to be carried out and this step adds to the mere ultrasound imaging scan.

Furthermore, in addition to the ultrasound scanner and to a probe tracking system, there is the need of a system allowing to optically scan the anatomic region of a patient and/or to extract the surface or the boundary of an organ or to draw the surface or the boundary. This introduces higher costs and renders the apparatus more complex and bulky.

SUMMARY OF THE INVENTION

An object of the present invention is to provide an ultrasound imaging system capable of combining morphological information related to the shape of the surface or the boundary of an anatomic region or of an organ.

According to a first aspect, an ultrasound imaging method is provided, which method comprises the steps of:

providing a digital representation of the shape of the surface or boundary of an anatomic region or of an organ;

acquiring an ultrasound image by ultrasound scanning the anatomic region or the organ;

combining the digital representation of the shape of the surface or boundary of the anatomic region or of the organ by:

registering the digital representation of the shape of the surface or boundary and the ultrasound image as a function of the difference in position of selected reference points on the digital representation of the surface or boundary and on the ultrasound image, the position of the reference points on the ultrasound image being determined by tracking the probe position at the reference points at the anatomic region or organ of a real body and in a spatial reference system in which the anatomic region or the organ of the real body is placed, wherein:

the digital representation is a three dimensional digital CAD model of the anatomic region or of the organ on which the reference points are defined;

the digital representation is morphologically non patient specific;

the shape of the surface or of the boundary of the model is modified to match the shape of the surface or of the boundary of the real anatomic region or the shape of the organ specific for a patient, as a function of the difference in position of the reference points in the digital CAD model and the position of the same reference points on the real anatomic region or on the real organ specific for the patient, the position of the reference points on the ultrasound image is determined by tracking the probe position at the reference points at the anatomic region or organ of a real body and in a spatial reference system in which the anatomic region or the organ of the real body is placed, the scanning for the acquisition of the ultrasound image of the anatomic region or of the organ being executed by moving the probe according to at least one scan path along at least part of the surface of the anatomic region or of the organ, the scan paths having a certain length, a certain shape and a certain width, the method comprising further the steps of tracking the probe position along the at least scan one path; and registering the data relatively to the position of the scan path, the length, the width and the shape of the scan path with the digital CAD model matched with the shape of the real anatomic region or of the real boundary;

graphically representing the at least one scan path on the digital CAD model of the anatomic region or of the organ matched to the real shape of the anatomic region or organ of a patient under examination;

the three-dimensional representation and the ultrasound image acquired being combined and saved; and the combination of three-dimensional representation and ultrasound image acquired being displayed and/or printed.

According to an embodiment, the three dimensional digital CAD model may comprise different anatomic regions of a body and encompass different organs, which are inside the region, a step being provided of selecting a part of the anatomical regions or of the organs to be used in carrying out the steps of the present method according to one or more of the preceding embodiments and variants.

According to a variant embodiment the three dimensional digital CAD model can represent the whole of the anatomic regions of a body and the whole of the organs in the body, a step being provided of selecting at least one or more of the anatomical regions or of the organs represented in the model to be used in carrying out the steps of the present method according to one or more of the preceding embodiments and variants.

According to still another embodiment, which can be provided in any combination with the previous embodiments, the tracking of the probe movements and position in the reference system comprises also the tracking of the probe orientation or the tracking of the orientation of the scan plane generated by the probe and the generation of a graphic representation of the shape of the probe and of its orientation in relation to the three-dimensional digital CAD model of the surface or of the boundary of an anatomic region or of an organ, the graphic representation of the probe being displayed in combination with the three-dimensional digital CAD model oriented and displaced along a scan paths accordingly to the orientation and displacement of the real probe along a scan paths on the surface of the anatomic region or the organ.

According to still another embodiment which can be provided in any combination with one or more of the preceding embodiments or variants, the step is provided of drawing or insert markers in the matched three dimensional digital CAD model, which markers are graphically distinguished from the digital cad representation of the anatomic region or of the organ and the graphic representation of these markers and/or the position on the digital CAD model being combined with the graphic representation of the three-dimensional digital CAD model and which markers being displayed together with the representation of the digital CAD model and which markers are saved on the combined image of the ultrasound image and of the three-dimensional CAD model matched to the real shape of the anatomic region or of an organ of the body of a patient.

Different modes of displaying the digital CAD model of an anatomic region or of an organ combined with the images representing the probe paths along said surface, optionally provided markers and the acquired ultrasound images.

According to one embodiment, the display screen may be divided in regions for displaying at the same time in different regions of the display, one beside the other, different views and in which at least in one display area there is shown the combined image of the anatomic region as modified by matching to the real anatomic region of the patient and of the tracking of the probe and or of the optionally inserted marker or markers.

According to a variant embodiment, the digital CAD model of an anatomic region or of an organ can be displayed as a three-dimensional image or as a two dimensional projection image of the three-dimensional digital CAD model on a two dimensional plane having a predefined orientation in relation to the three-dimensional digital CAD model.

In a further variant embodiment of the above, in at least one further area of the display areas there is displayed the ultrasound image along one selected scan plane intersecting or passing through the position identified by at least one of the markers or having a predetermined position and orientation relatively to the at least one of the markers.

According to still a further variant embodiment still a further display area of the display may be provided in which the ultrasound image along a further selected scan plane intersecting or passing through the position identified by at least one of the markers or having a predetermined position and orientation relatively to the at least one of the markers and which position and or which orientation is different from other scan planes of which the ultrasound images are shown in at least one or further display areas.

A further embodiment of the present invention provides the steps of carrying out a further ultrasound imaging scan of the same patient and of the same anatomic region or of the same organ in a second time following the time of a previous ultrasound imaging scan, the steps comprising:

retrieving the image of the three-dimensional digital CAD model of the anatomic region combined with the images of the one or more scan paths carried out and with the ultrasound images acquired along the scan planes and with optionally inserted mat least one markers;

displaying superimposed to the combined images the set of selected reference points;

registering the shape of the surface of the anatomic region and or of the organ with the shape of the three dimensional representation of the anatomic region or the organ by the retrieved combined image as a function of the differences of the position of one or more of the reference points on the combined image and the position of the points determined by tracking the probe position at the reference points provided on the surface of the anatomic region or organ of the real body of the patient;

tracking the probe position and orientation in a reference system in which the anatomic region or the organ is placed and positioning the probe at the at least one or more markers for generating ultrasound image data of the same object as in the previous ultrasound image data scan and along at least one identical scan plane having one identical orientation relatively to the scan plane of the previous ultrasound imaging scan;

comparing the images obtained in the previous ultrasound imaging scan at the same marker point with the ones obtained in the second following ultrasound imaging scan;

displaying the ultrasound image according to one or more of the variant embodiments described above.

Additional steps may include saving these additional ultrasound images in combination with the three-dimensional digital CAD model of the anatomic region and/or organ and in combination with the scan paths of the probe and eventually with the one or more markers.

It should be noted that the embodiments shown do not request scanning with optical means an anatomic region, so that this method is easily applied also to internal organs for which no optical scan of the surface or boundary may be obtained.

According to an additional aspect, an ultrasound imaging system is provided comprising:

a probe comprising electro-acoustic transducer grouped as one array of transducers;

the transducers generating ultrasound signals upon excitation by electric driving signal and generating electric signals upon receipt of reflected ultrasound signals;

an ultrasound signal processing unit configured to receive the signals generated by the reflected ultrasound signals falling on the transducers and to process the signals for generating image data related to the target body in which the reflectors of the ultrasound transmitted signals are provided;

a probe tracking system configured to determine the position of the probe in a space describe by a spatial reference system and further to determine the orientation of a scan plane generated by the probe;

a memory in which a three-dimensional digital CAD model of at least one anatomic region or of at least one organ is stored and from which the model can be retrieved and loaded in a graphic processor;

a graphic processor configured to process the image data of the three-dimensional digital CAD model and the ultrasound image data generated by the ultrasound signal processing unit;

the graphic processor receiving the probe position and orientation data and generating a virtual model of the probe and graphic representations of the traces of the path of the probe along one or more scan paths;

an input interface for defining the position of one or more reference points in relation to the shape of the surface of the anatomic region or the organ represented by the digital CAD model;

a processor configured to process the difference in position of the probe at the position of the reference points on the surface of the anatomic region of the organ of the real body and configured to modifying the shape of the surfaces of the anatomic region or the organ of the three-dimensional digital CAD model as a function of said difference in position of the reference points positioned on the three-dimensional digital CAD model and on the real anatomic region or the real organ;

the graphic processor being configured for registering the modified three-dimensional digital CAD model with the representation of the traces of the scan paths of the probe along the surface of the anatomic region or of the organ and the ultrasound images generated from each scan paths and configured for combining the image data in a combined image;

a display connected to the graphic processor output and which display is configured to display the combined images processed by the graphic processor.

According to an embodiment, which can be provided in combination with the above, the ultrasound system further comprises a memory in which three-dimensional digital CAD models of different anatomic regions of a body and/or of different organs are stored which models can be retrieved and loaded in the graphic processor for being processed according to one or more of the different embodiments of the above described method, the system further comprising a user interface including a selector for selecting models of at least one anatomic region or organ and for loading the selected model in the graphic processing unit.

According to a variant embodiment, which can be provided in combination or alternatively with the previous one, there is provided a memory in which a three-dimensional digital CAD model of the complete body is stored, the system further comprising a user interface including a selector for selecting the parts of the model representing at least one anatomic region or at least one organ and for loading the selected parts of the model in the graphic processing unit.

According to still another embodiment, which can be provided in combination with one or more of the preceding embodiments, the system further comprises input means for drawing or setting markers at specific position on the three-dimensional digital CAD model of the at least one anatomic region or the at least one organ.

According to another embodiment, the system includes a memory for storing a combined image comprising the three-dimensional digital CAD model of the at least one anatomic region or the at least one organ after having been modified for matching the real shape of the real anatomic region of the body of the patient, and in combination therewith the ultrasound image data of the anatomic region or of the organ, the traces of the scan paths of the probe along the surface of the anatomic region or organ registered with the shape of the anatomic region or of the organ represented by the model, optional markers set by the user for distinguishing and highlighting the position of relevant structures or features in the ultrasound images;

a user interface for addressing the memory and retrieving the combined image and displaying on the display; and input means for setting on the combined image reference points for carrying out the registration of the shape of the surface of the real anatomic region of the body of a patient or of the real organ with the shape represented in the combined region.

According to an embodiment, the system is provided with a memory for saving a sequence of combined image each comprising the three-dimensional digital CAD model of the at least one anatomic region or the at least one organ after having been modified for matching the real shape of the real anatomic region of the body of the patient and in combination therewith the ultrasound image data of the anatomic region or of the organ, the traces of the scan paths of the probe along the surface of the anatomic region or organ registered with the shape of the anatomic region or of the organ represented by the model, optional markers set by the user for distinguishing and highlighting the position of relevant structures or features in the ultrasound images acquired or set at different times.

According to the above embodiments the following functions can be obtained.

Only one model of the anatomic region or of the organ is needed which must not be separately acquired by an optical scanning system.

The model is a digital CAD model which has standard shapes or configurations of the anatomic regions and of the organs, and the shape of the surfaces defined by the model are modified in order to match le morphology of the real anatomic region and/or the real organ of a patient.

Combining the ultrasound image data with the information of the model and furthermore representing graphically the scan paths of the probe along the surface of the anatomic region or organ allows to show in a visual manner which parts has been effectively scanned and which parts has not been scanned or scanned only once.

Due to the possibility to recall combined images of previous ultrasound scanning sessions and to draw on the three dimensional model markers of points of interest within the ultrasound image data, it is possible to easily carry out follow up examinations. When the previous combined image is displayed on the display the probe can easily be positioned on the real anatomic region of a patient or on the real organ by simply displacing the probe such that the image of the probe represented on the display and driven by the tracking system coincides with the corresponding marker.

Due to this feature, if once in time a lesion is found, it is possible to reposition the probe exactly at the position at which the same lesion is imaged without the need of carrying out various scans for finding where the lesion is.

Reduction of time and certainty to acquire images of the same lesion are ensured so that follow up analysis can be carried out very quickly and with a high certainty to have imaged the same object so that diagnosis has a high level of reliability.

By providing a model of the body, which encompasses more than one anatomic region, it is furthermore possible to add data to a loaded model and to extend also in a follow-up session the process according to the present method and system to adjacent anatomic regions or organs.

According to another embodiment, a Breast Imaging-reporting and Data system (sometimes shortened to BI-RADS) may be provided in combination with one or more of the preceding embodiments or variants.

Breast Imaging-Reporting and Data System is a quality assurance tool originally designed for use with mammography. The system is a collaborative effort of many health groups but is published and trademarked by the American College of Radiology (ACR). The system is designed to standardize reporting, and is used by medical professionals to communicate a patient's risk of developing breast cancer. The document focuses on patient reports used by medical professionals, not "lay reports" that are provided to patients. The BI-RADS is published by ACR in the form of the BI-RADS Atlas. As of 2013 the Atlas is divided into 3 publications: Mammography, Fifth Edition; Ultrasound, Second Edition; Mill, Second Edition. (see also https://en.wikipedia.org/wiki/BI-RADS).

Automatic parsers have been developed to automatically extract BI-RADS features categories and breast composition from textual mammography reports. (see also Nassif, Houssam; Woods, Ryan; Burnside, Elizabeth; Ayvaci, Mehmet; Shavlik, Jude; Page, David (2009). "Information Extraction for Clinical Data Mining: A Mammography Case Study" (PDF). IEEE International Conference on Data Mining (ICDM'09) Workshops. Miami: 37-42; Nassif, Houssam; Cunha, Filipe; Moreira, Ines C; Cruz-Correia, Ricardo; Sousa, Eliana; Page, David; Burnside, Elizabeth; Dutra, Ines (2012). "Extracting BI-RADS Features from Portuguese Clinical Texts" (PDF). IEEE International Conference on Bioinformatics and Biomedicine (BIBM'12): 539-542. PMC 3688645. PMID 23797461; Sippo, Dorothy A; Warden, Graham I; Andriole, Katherine P; Lacson, Ronilda; Ikuta, Ichiro; Birdwell, Robyn L; Khorasani, Ramin (2013). "Automated Extraction of BI-RADS Final Assessment Categories from Radiology Reports with Natural Language Processing". Journal of Digital Imaging. 26 (5): 989-994. doi:10.1007/s10278-013-9616-5. PMC 3782591; Percha, Bethany; Nassif, Houssam; Lipson, Jafi; Burnside, Elizabeth; Rubin, Daniel (2012). "Automatic classification of mammography reports by BI-RADS breast tissue composition class" (PDF). Journal of the American Medical Informatics Association (JAMIA). 19 (5): 913-916. doi:10.1136/amiajnl-2011-000607. PMC 3422822. PMID 22291166.)

BI-RADS is a quality control system, in day-to-day usage. The term "BI-RADS" refers to the mammography assessment categories. These are standardized numerical codes typically assigned by a radiologist after interpreting a mammogram. This allows for concise and unambiguous understanding of patient records between multiple doctors and medical facilities. The assessment categories were developed for mammography and later adapted for use with MRI and Ultrasound findings. The summary of each category, given below, is nearly identical for all 3 modalities.

0: Incomplete
1: Negative
2: Benign
3: Probably benign
4: Suspicious
5: Highly suggestive of malignancy
6: Known biopsy—proven malignancy An incomplete (BI-RADS 0) classification warrants either an effort to ascertain prior imaging for comparison or to call the patient back for additional views and/or higher quality films. A BI-RADS classification of 4 or 5 warrants biopsy to further evaluate the offending lesion. Some experts believe that the single BI-RADS 4 classification does not adequately communicate the risk of cancer to doctors and recommend a sub-classification scheme:

4A: low suspicion for malignancy, about 2%
4B: intermediate suspicion of malignancy, about 10%
4C: moderate concern, but not classic for malignancy about 50%.

BI-RADS also provides categories of breast composition:
The breasts are almost entirely fatty
There are scattered areas of fibroglandular density
The breasts are heterogeneously dense, which may obscure small masses
The breasts are extremely dense, which lowers the sensitivity of mammography.

According to the present embodiment the following steps are provided:
setting the spatial position of a target in an US image; and
analyzing the contour of the echogenicity around the target in an automatic way giving BI-rads automatic score of the defined target.

According to a variant embodiment, the analysis can be carried out on a 2D image.

An additional variant embodiment a 3D Volume around the target can be acquired and can be analyzed for better geometric shape recognition and BI-RADS score determination.

BRIEF DESCRIPTION OF THE DRAWINGS

The features of the present method for ultrasound imaging and of the system for carrying out the method are described in several examples referring to exemplary embodiments shown in the enclosed figures.

Although the examples refer to a typical case in which the anatomic region is the breast, so that no internal organ is subjected to the present method, it appears clearly that because there is no need to obtain a three-dimensional optical scanning of an organ or an anatomic region of a body, the method can be easily applied also to organs which are completely embedded in the tissues of the body.

The exemplary embodiments are illustrated in the following figures:

FIG. 1 shows a high level block diagram of an embodiment of a system according to the present invention.

FIGS. 2 to 4 show the flowcharts representing embodiments of the method according to the present invention.

Figure 5A:
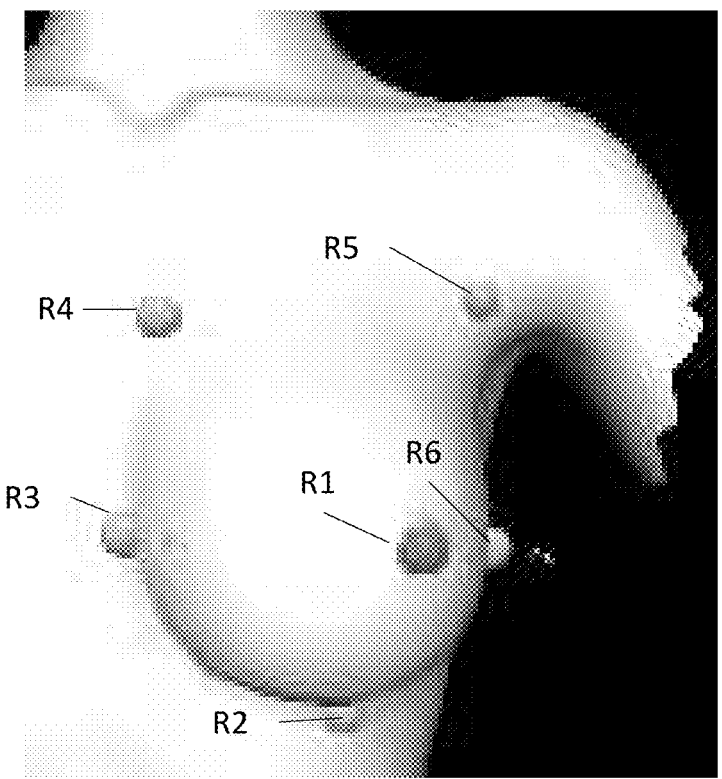
Figure 5B:
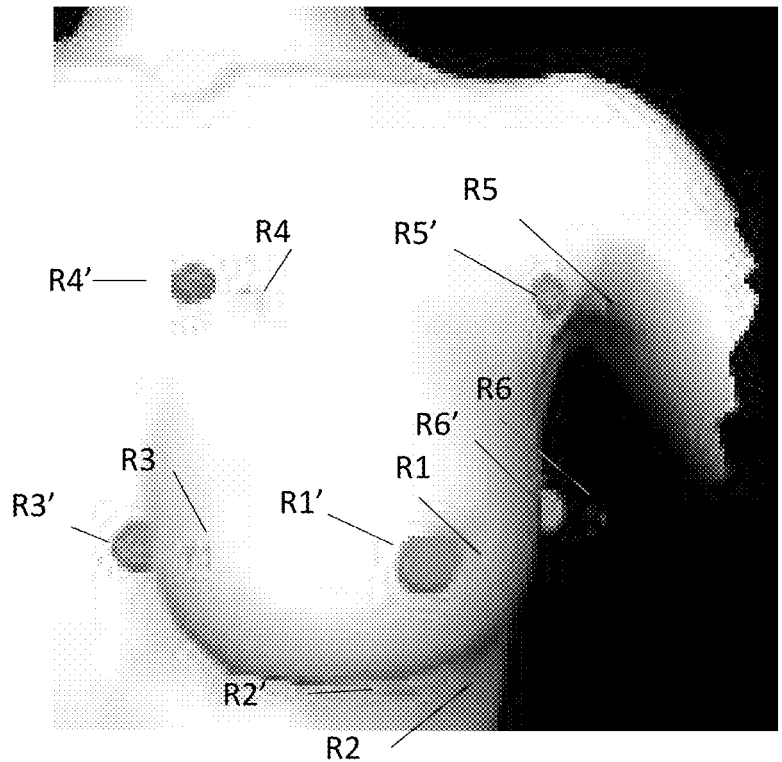

FIG. 5*a* and FIG. 5*b* represent the shape of the anatomic region of the breast as represented in a three-dimensional digital CAD model and relating to the real shape of the breast of a patient both representations being provided with reference points for modifying the shape of the breast in three-dimensional digital CAD model at the shape of the breast in the real patient body.

Figure 6:
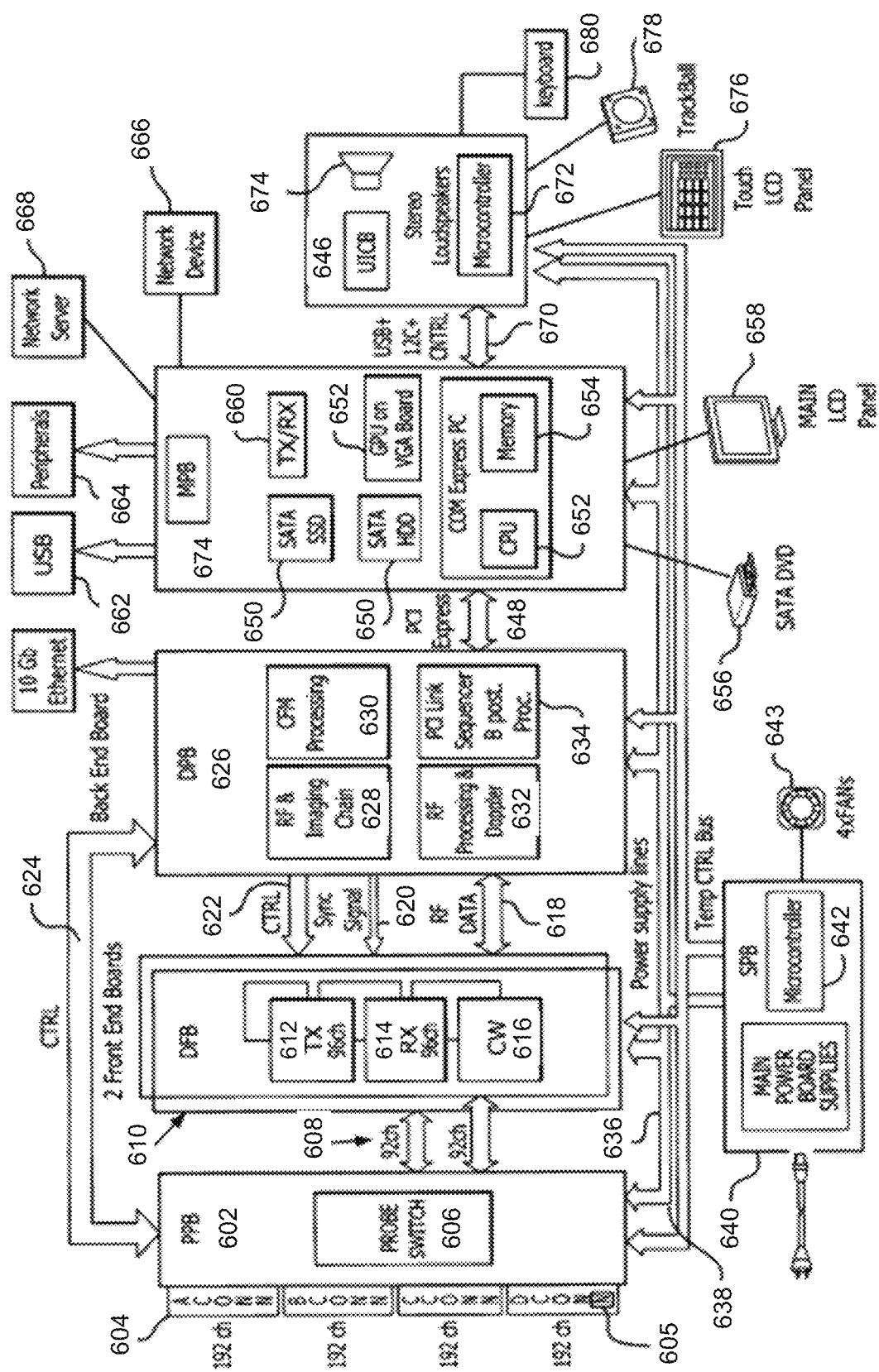

FIG. 6 illustrates a block diagram of an ultrasound system according to the invention.

Figure 7:
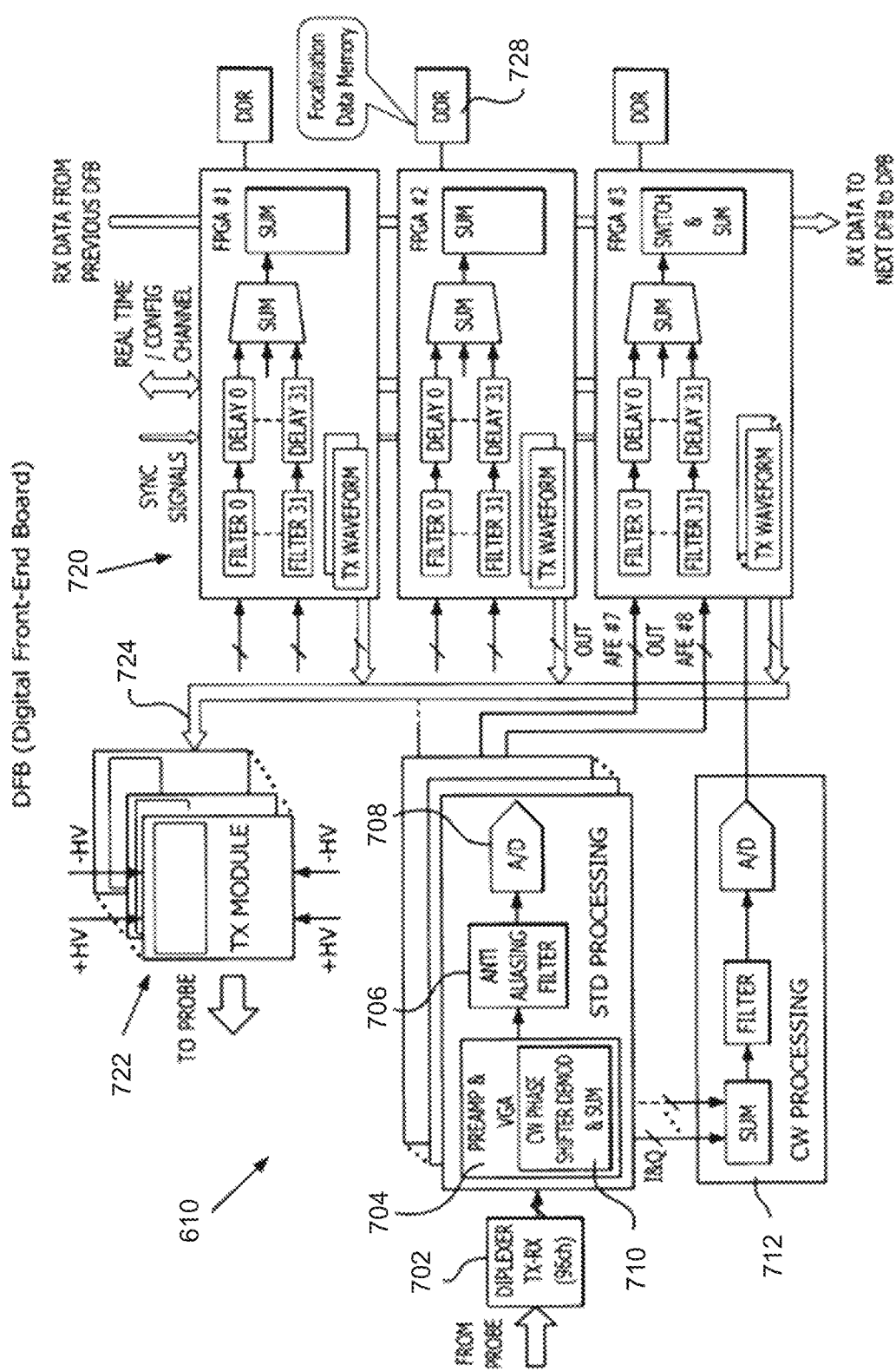

FIG. 7 illustrates a block diagram of a portion of the digital front-end boards.

Figure 8:
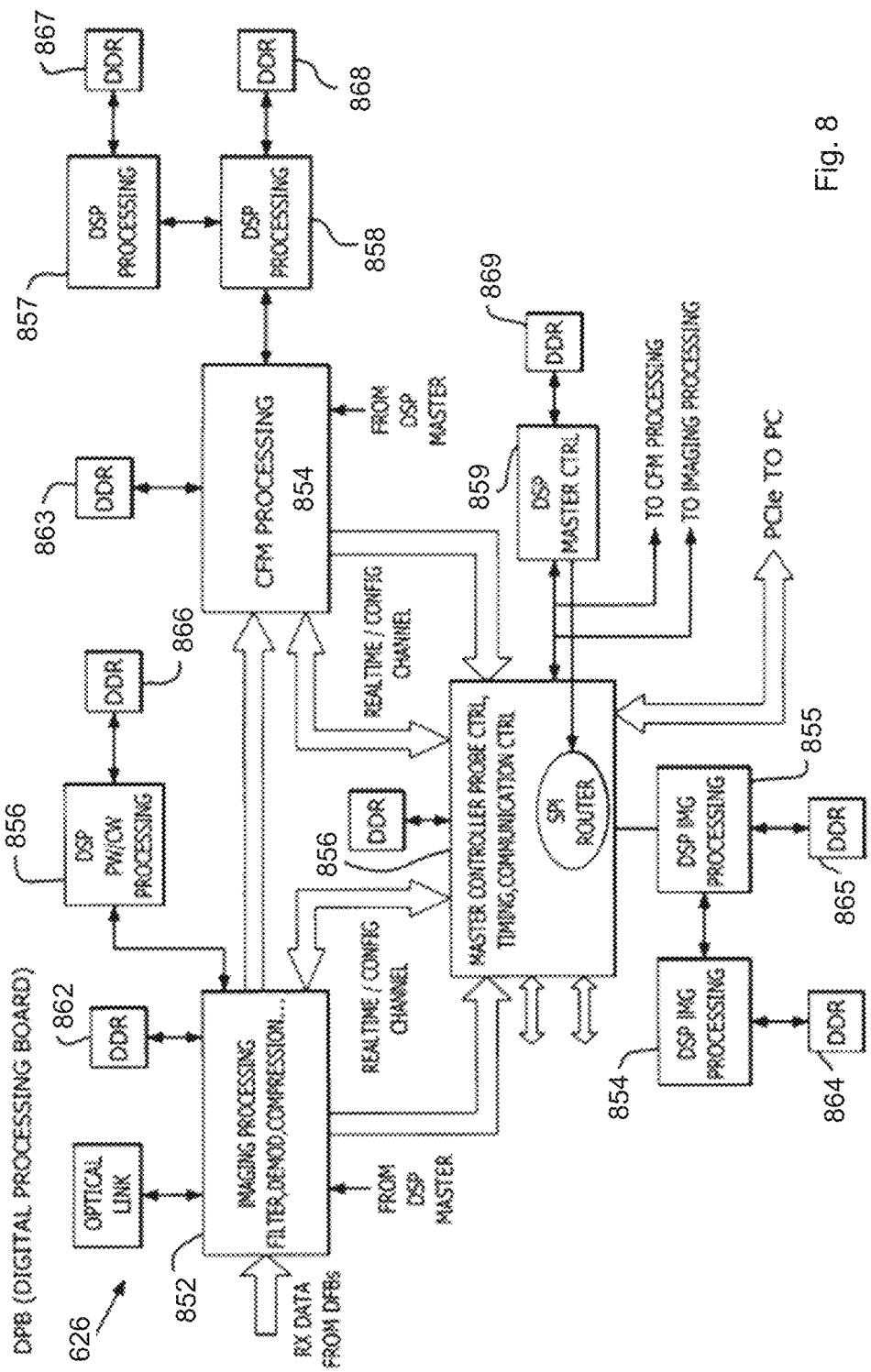
Figure 9:
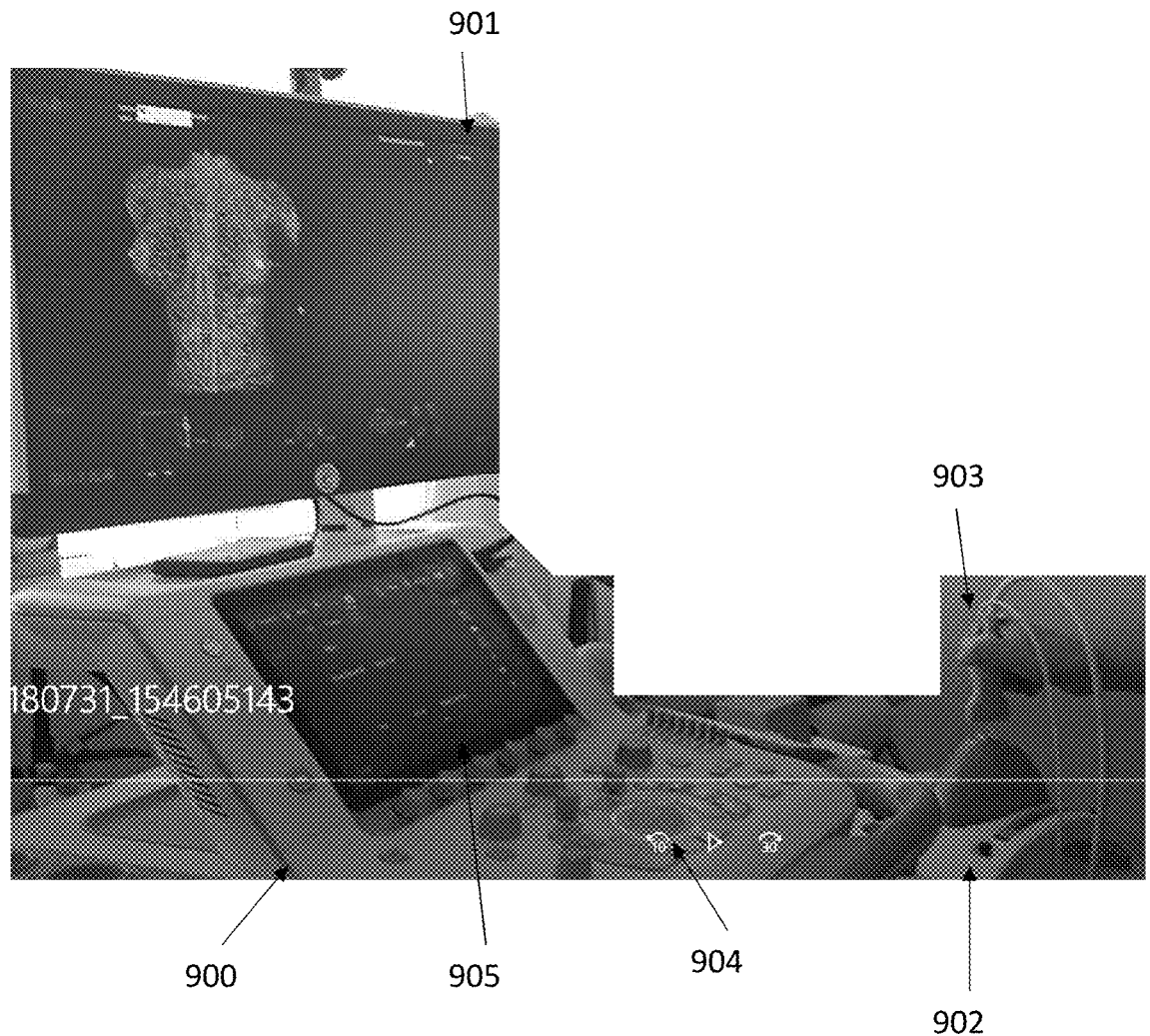
Figure 10:
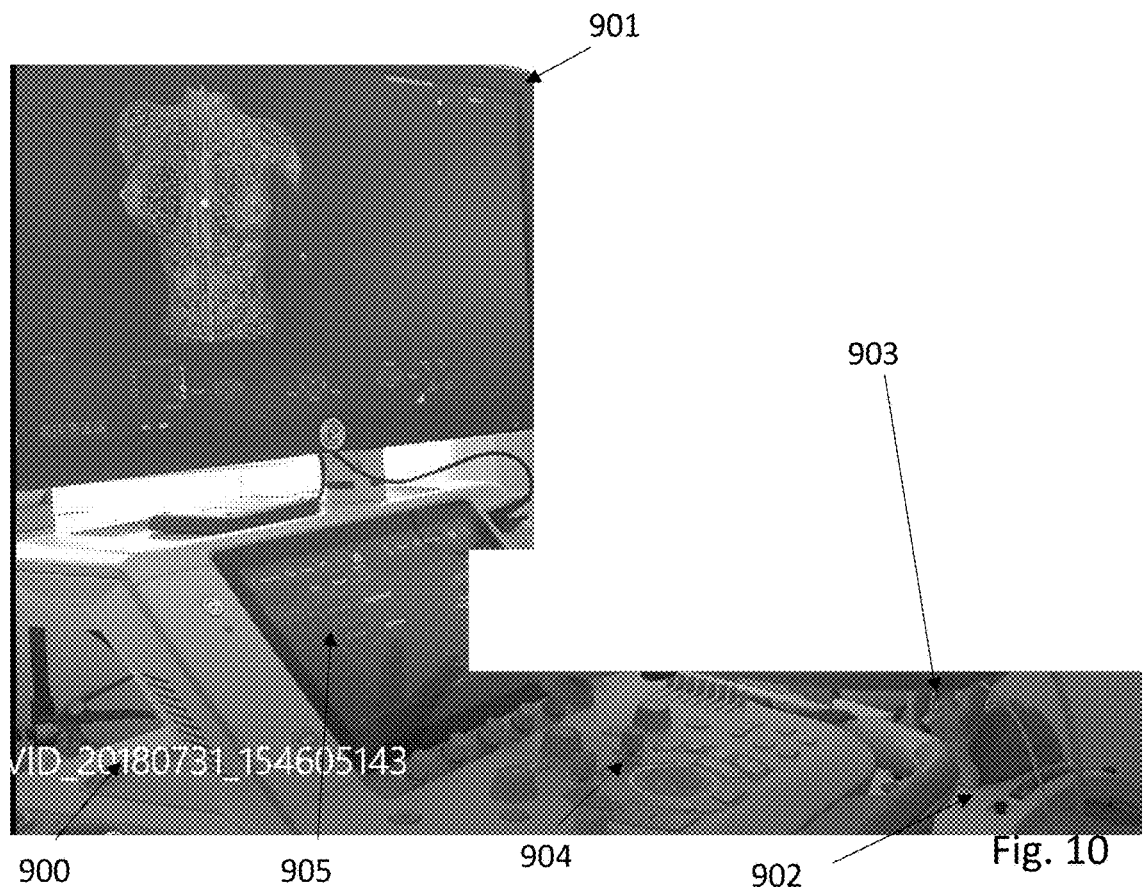
Figure 11:
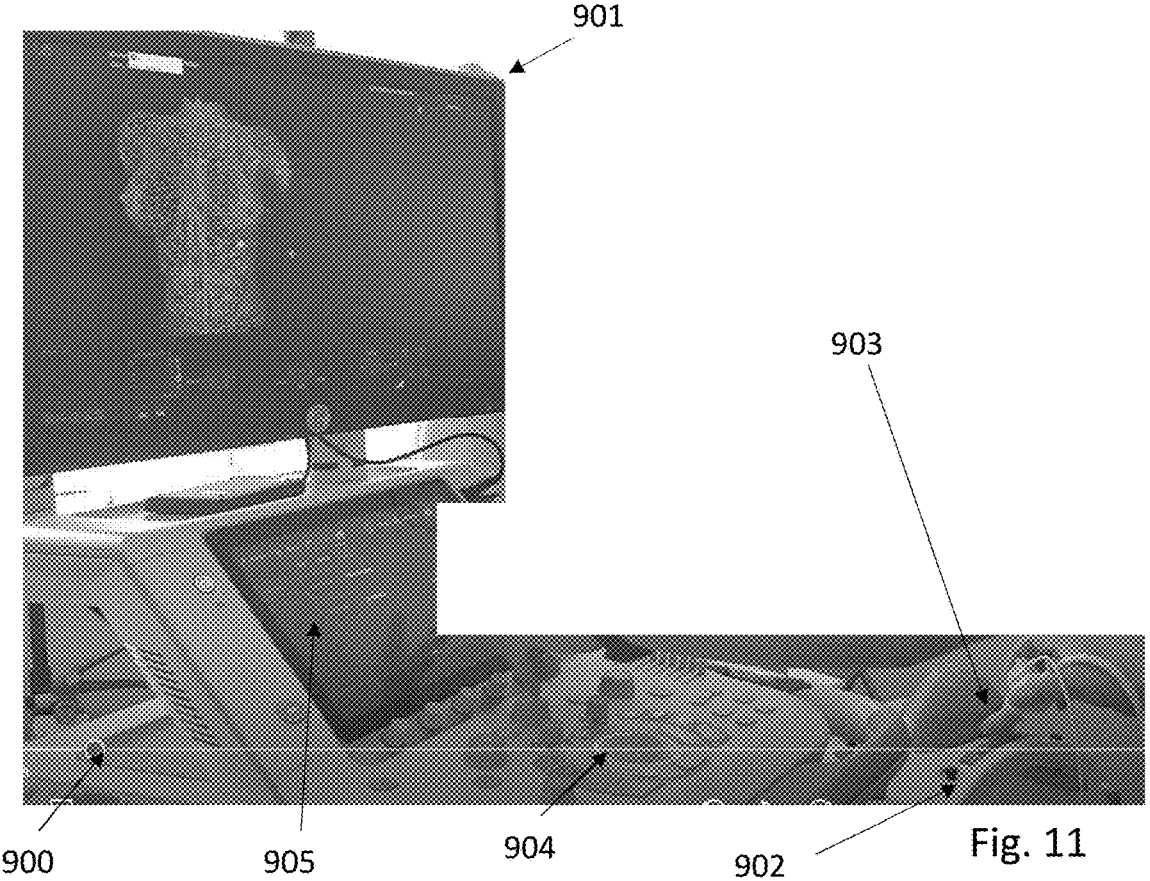
Figure 12:
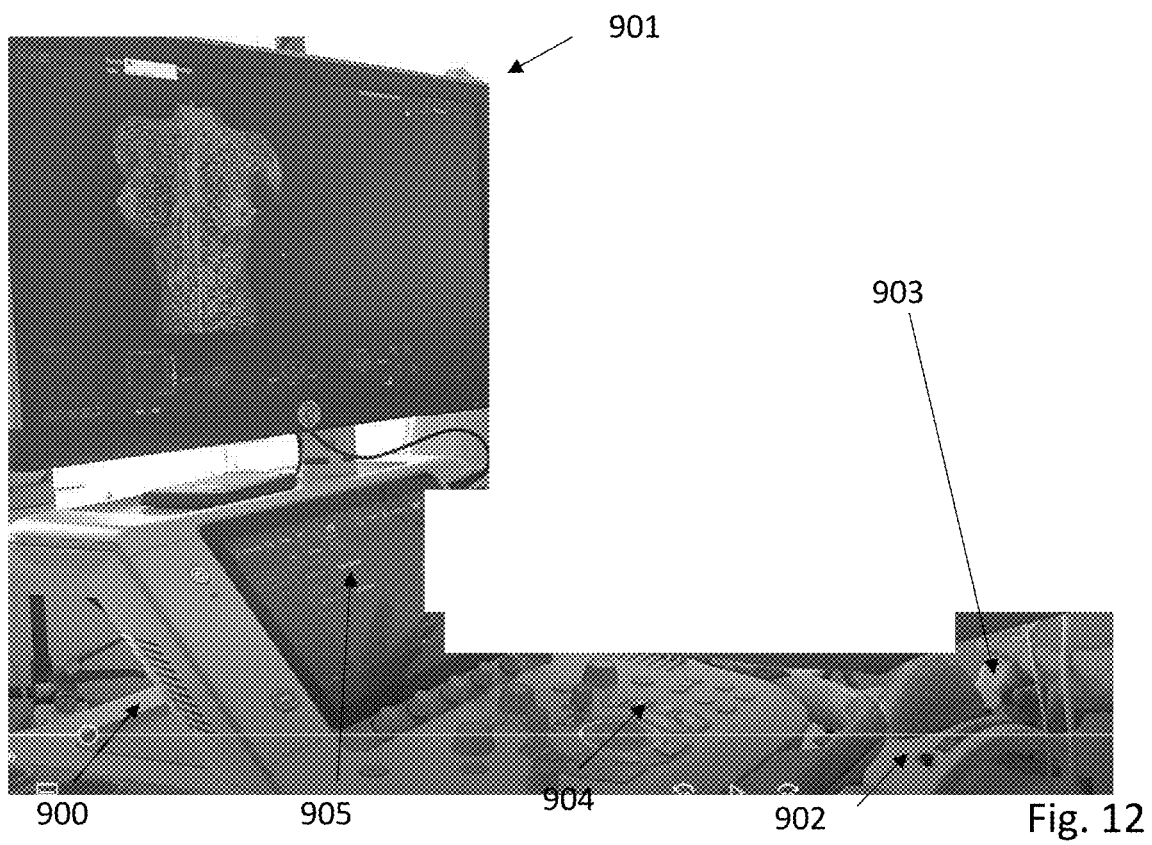
Figure 13:
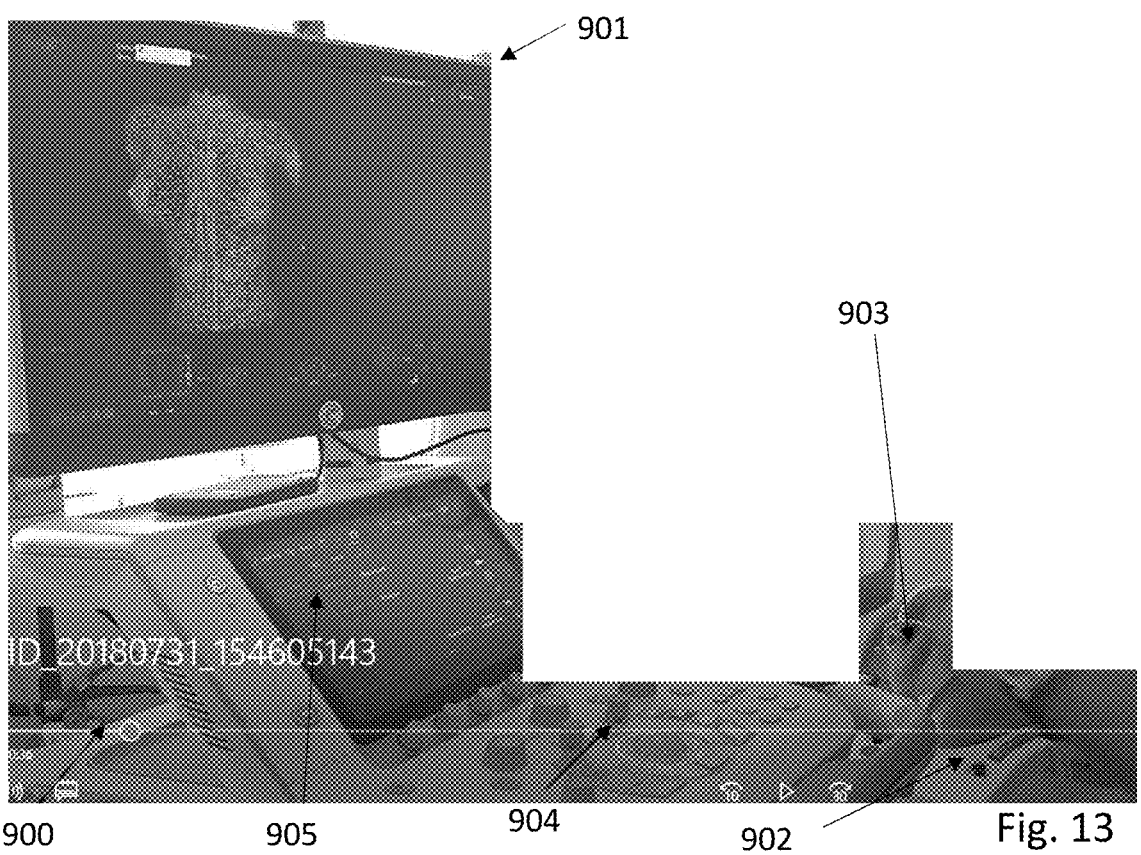
Figure 14:
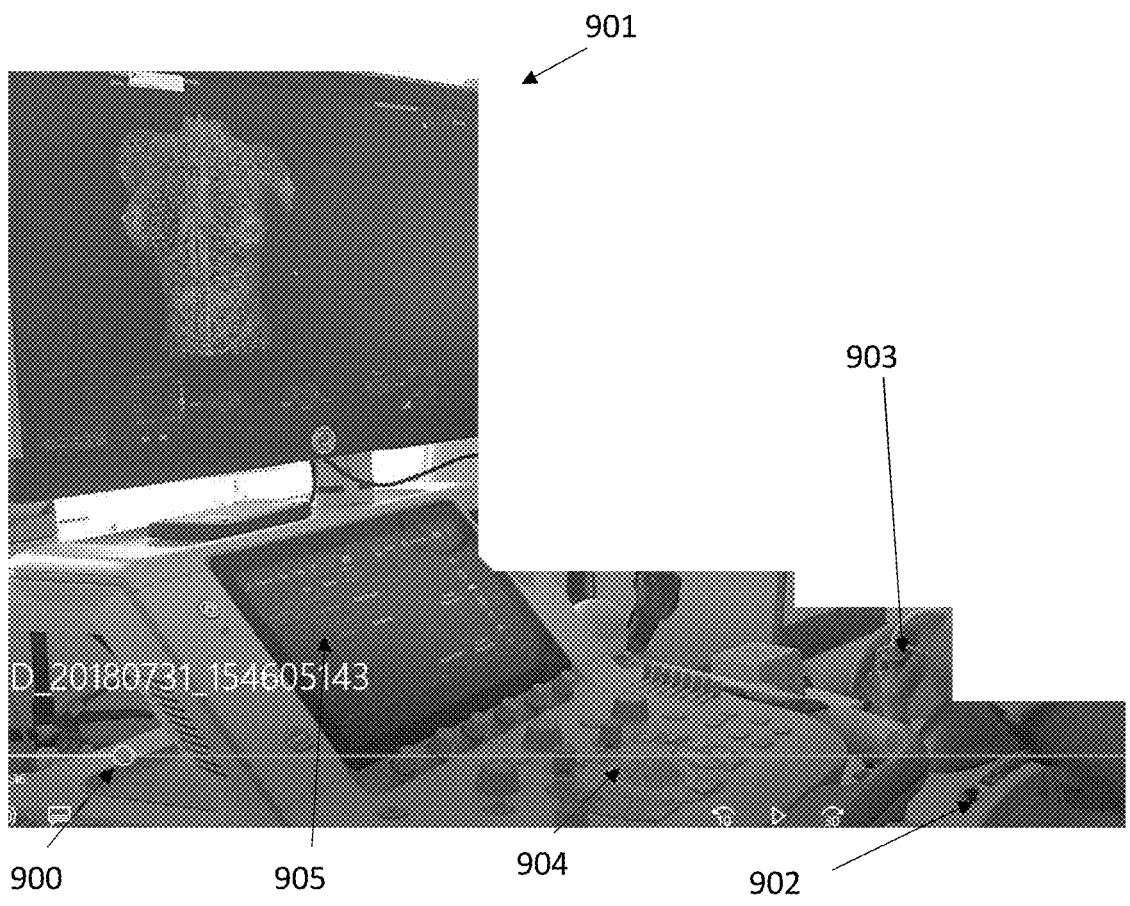
Figure 15:
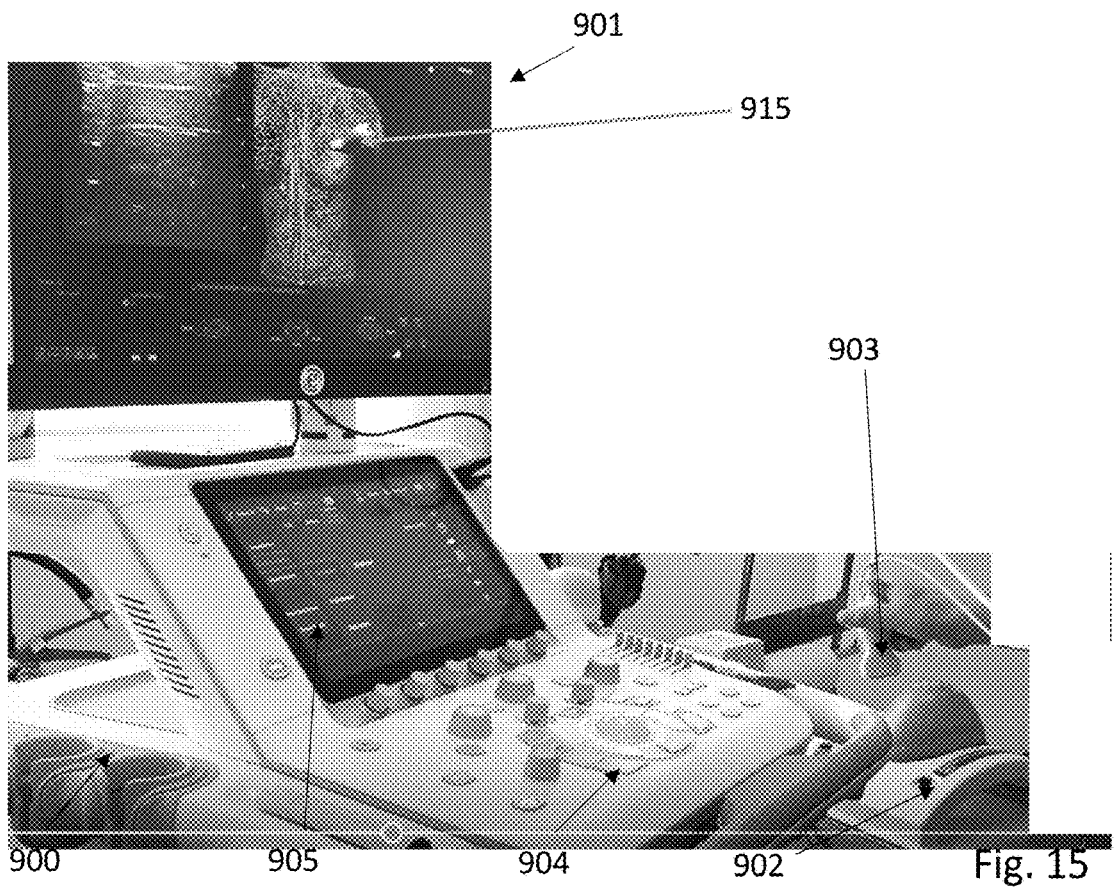

FIG. 8 illustrates a block diagram of the digital processing board.

FIGS. 9 to 14 show an ultrasound imaging system according to an embodiment respectively in each of the phases for registering the position of the reference point on the three-dimensional digital CAD model with the same reference points on the breast of a patient which in the present case is represented by a replica of a breast associated to a probe tracking system.

FIGS. 15 to 20 show the steps of carrying out imaging scans of the breast along different scan paths and the representation of the scan paths on the model while the ultrasound image data is registered with the model.

Figure 21:
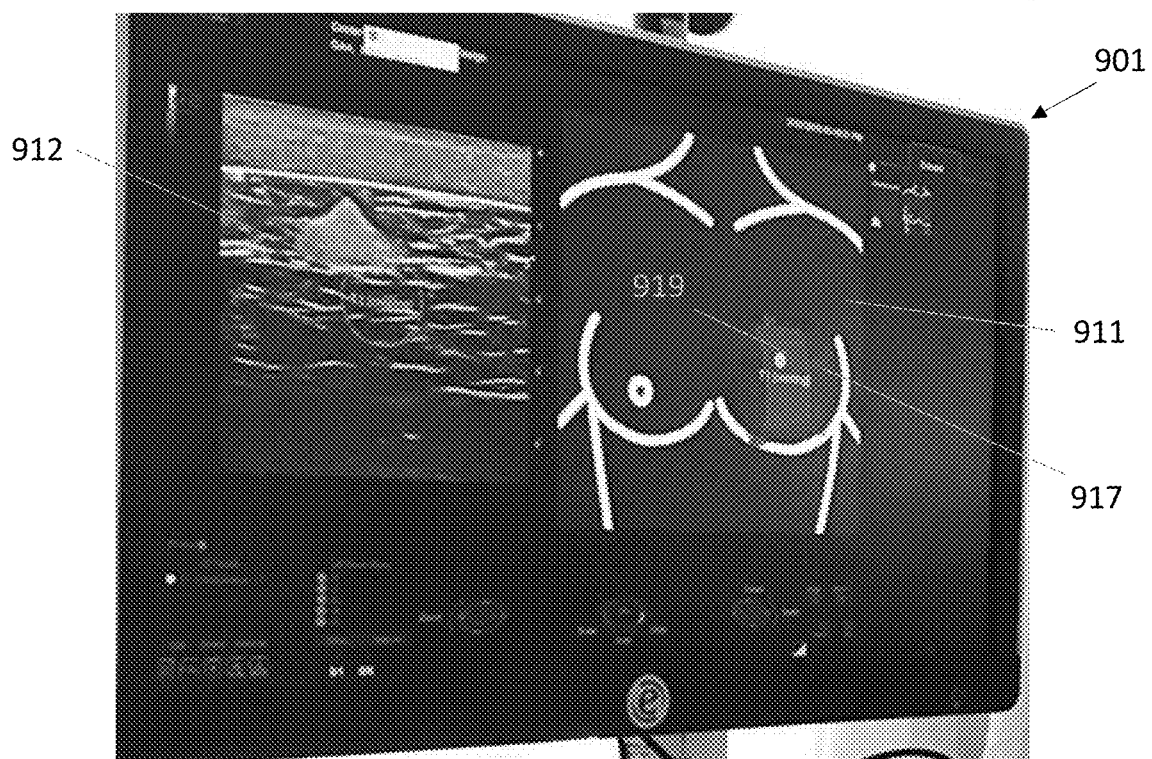

FIG. 21 shows the ultrasound system according to the previous figures and the drawing of a marker on the combined image on the display of the scanner.

Figure 22:
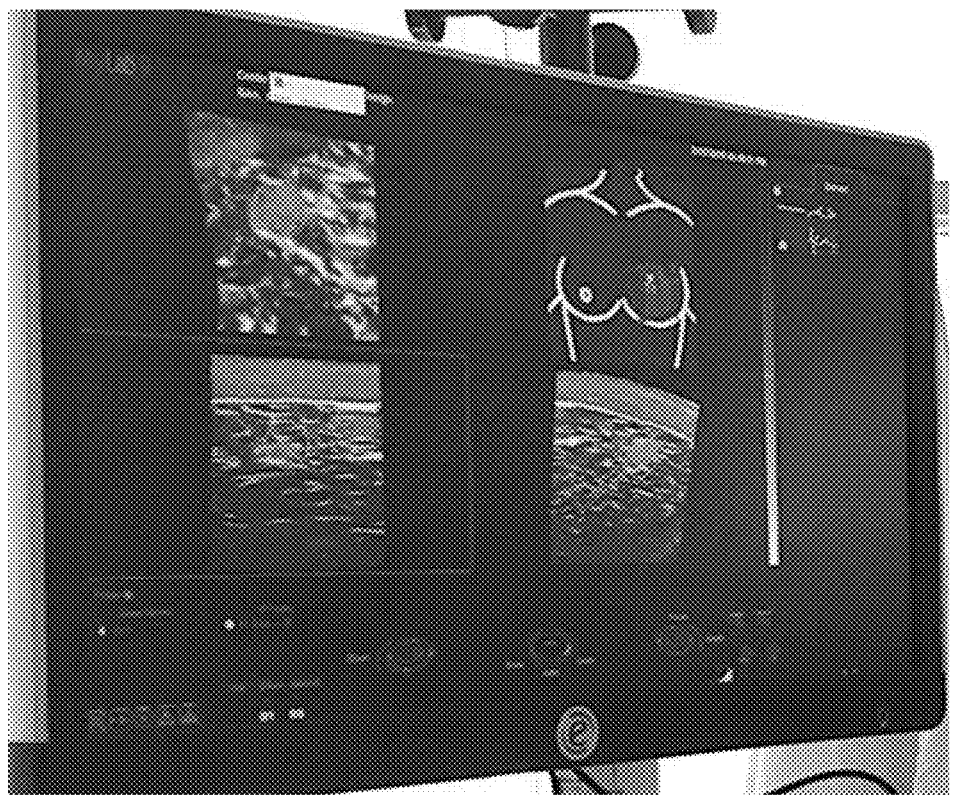

FIG. 22 show a different example of embodiment of a display mode of the combined image acquired according to the present method.

Figure 23:
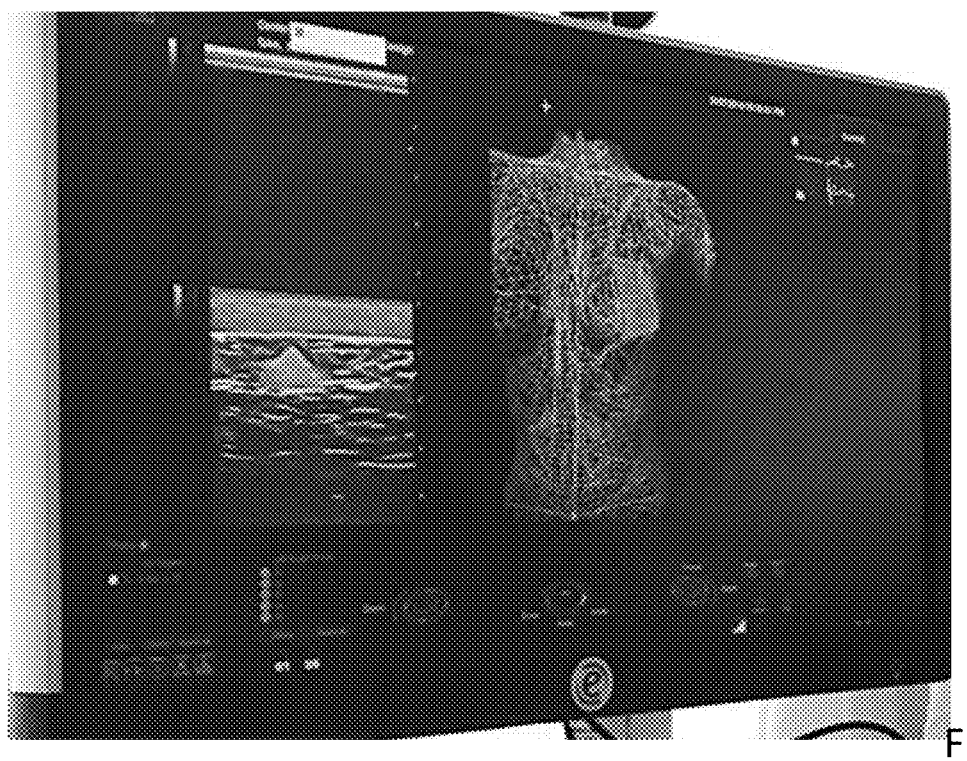
Figure 24:
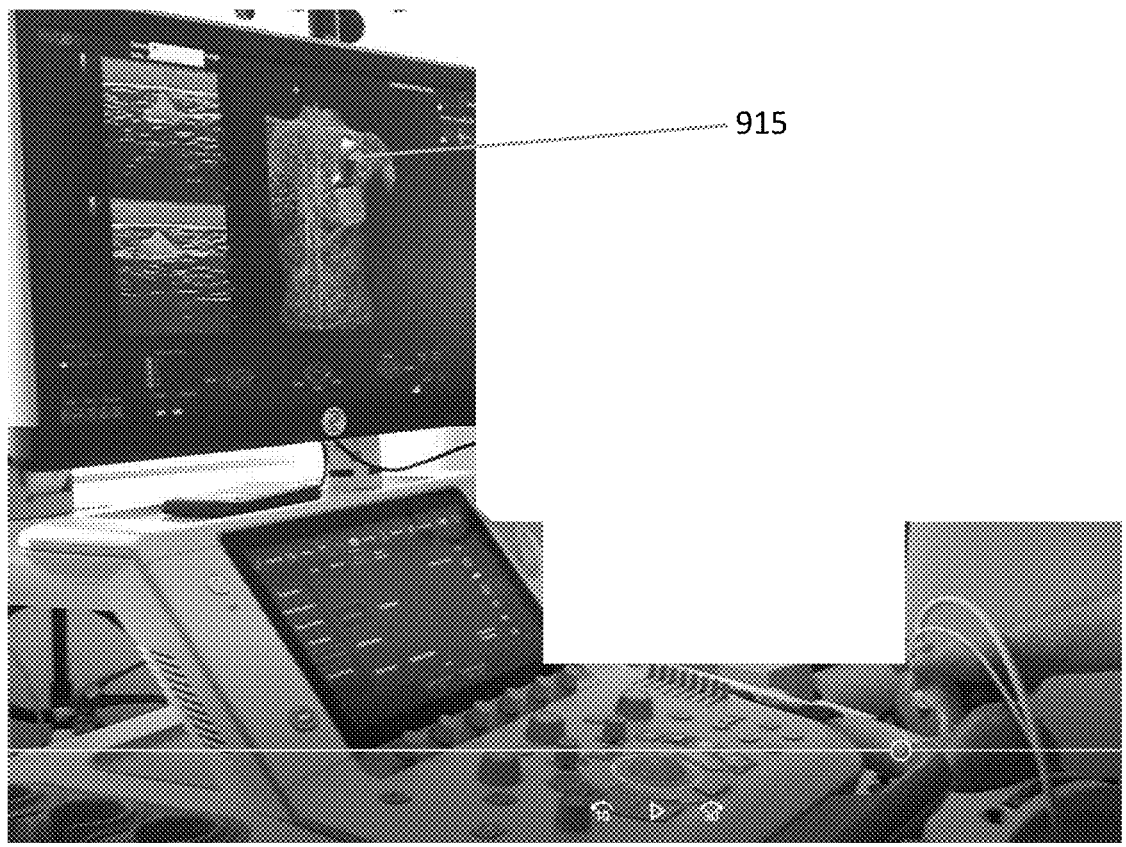

FIGS. 23 and 24 show exemplary embodiments of carrying out a follow up ultrasound imaging session of the breast of a same patient.

Figure 25:

FIG. 25 show the steps of extending the ultrasound imaging method to adjacent anatomic regions of the breast.

DETAILED DESCRIPTION OF EMBODIMENTS OF THE INVENTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

FIG. 1B illustrates a high-level block diagram of an ultrasound system implemented in accordance with embodiments herein. The ultrasound machine for acquiring diagnostic images comprises a probe 151 provided with an array of electroacoustic transducers intended to transform excitation electric signals sent thereto into ultrasound acoustic signals and vice versa to transform the received acoustic signals into corresponding electric signals.

A transmit section and a receive section 152, 153 are connected alternatively to one another with the probe to provide to each individual transducer an excitation signal of the corresponding ultrasound pulse and to receive the electric signal corresponding to an acoustic pulse that has hit the transducer.

The receive signals of the transducers are each one sent in an independent manner through a dedicated channel or by a multiplexer to an analog digital converter (not shown) that samples said signals with a predetermined sampling rate and it provides output digitized receive signals of each transducer/channel.

Therefore, digitized signals are subjected to a processing by a beamforming processor 155 that carries out the time alignment of the contributions of the receive signal of each channel correspondingly to the travel time of the signal reflected by a predetermined reflection point from said reflection point to the corresponding transducer.

Since the individual transducers of the array provided on the probe have positions different from each other, they necessarily have different distances from the reflection point and therefore the echo signal deriving from such point reaches each individual reflector in a different moment. The focusing process performs the time re-alignment of the contributions of the receive signal of each transducer deriving from the same reflection point and therefore sums together such contributions in a coherent manner. The process is repeated for each datum along each line forming a two-dimensional or three-dimensional image. In the beamforming process, the receive signals are subjected to time re-alignment and phase shift equalization. The signals obtained by the coherent sum of the time re-aligned contributions of the individual transducers and by the coherent combination of the receive signal contributions along a receive line position or line of sight due to differently laterally shifted transmit beams encompassing the receive line position or line of sight are provided to a processing section 156 for generating images according to different modes such as B mode, Doppler, color Doppler, etc. that then are transmitted to a scan converter 157 in order to generate images that can be displayed, printed, stored or subjected to other image processing.

According to the present embodiment the further image processing of the scan converted ultrasound images is carried out by a Graphic subsystem 154. This graphic subsystem is configured to further process image data as will be explained in the following and according to one or more embodiments of the method described in the above paragraphs. The output of the graphic subsystem 154 is connected to a display 158 and or to other devices such as printers or storage devices either of the external and removable kind or internal and not removable such as hard disks or similar devices.

A centralized control unit 159 governs the workflow of the above mentioned units in a synchronized manner in order to obtain the aimed functions.

Figure 1:
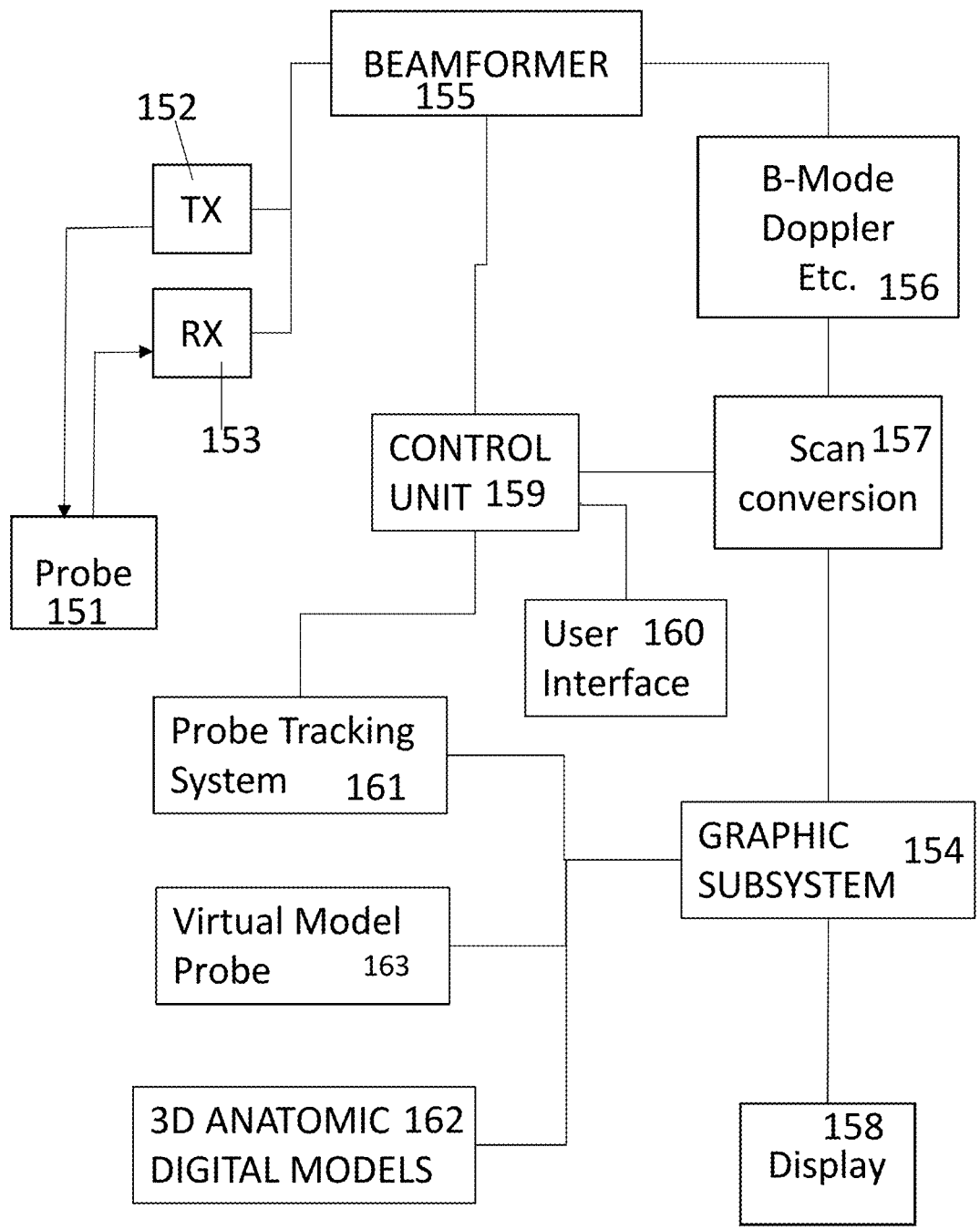

As it appears from the FIG. 1 in the present embodiment the control unit 159 is connected to a user interface 160 which can include any time of mmi units (man machine interfaces) allowing to input data or commands to the system through the control unit 159 or to carry out other tasks as for example diagnostic tasks.

The position and the displacement as well as the orientation of the probe in space and relatively to the anatomic region or organ to be scanned are determined by a probe tracking system 161. This kind of system is known at the state of the art and is commonly used in ultrasound systems.

Further to the tracking system 161, memories 162, 163 are provided. In a first memory indicated by 162, 3D digital CAD models of at least one or for more anatomic regions are stored and ready to be recalled and loaded in the buffer of the graphic subsystem 154 and in a further one 163 there might be stored virtual images of the probe which will be displayed combined with the model and the ultrasound image data as it will explained in the following.

Figure 2:
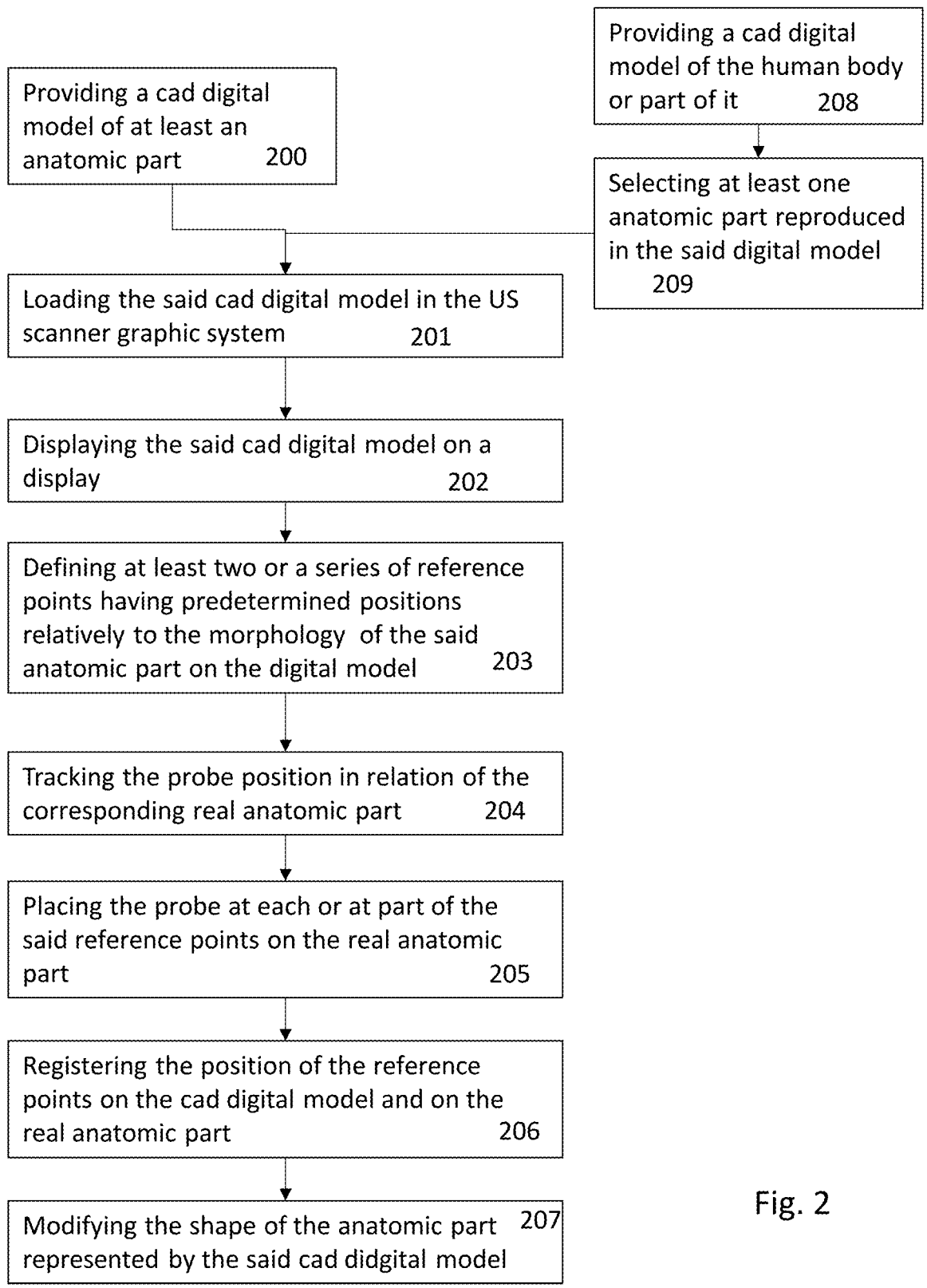

FIG. 2 shows a flowchart of an embodiment of the method according to the present invention, which is carried out by the system according to the example of FIG. 1.

At step 200, a digital representation of at least an anatomic region or of at least an organ is provided. Such digital model is in the form of a CAD file and is stored in a memory 162. The model is recalled from the memory 162 and loaded at step 201 in the graphic subsystem 154.

At step 202, the three-dimensional digital CAD model is displayed on the display 158 of the ultrasound imaging system. At step 203, by means of the user interface 160, the user can define at least two or a series of reference points (indicated as RP 1 to RP6 in FIGS. 5a and 5b). This reference points have predetermined positions relatively to the morphology of the anatomic region represented on screen by the digital model.

The following step consists in registering the position of the reference points in the digital CAD model and on the real anatomic part to be examined, in this case the breast. This has been accomplished in 204 by tracking the probe at the position of the reference points determined in relation to the morphology or the shape of the real anatomic region to be examined. These steps provide for placing the probe at each or at some of the reference points on the real anatomic region to be examined as indicated by the step 205.

The data obtained for the position of each reference point on the three-dimensional digital CAD model and on the real anatomic region is used for registering the reference points one with relatively to the other and thus determines a deformation of the shape of the anatomic region as represented by the three-dimensional digital CAD model such that the shape is modified to match the shape of the real anatomic region as indicated at step 207.

Steps 208 and 209 describe a possible alternative way of providing the three-dimensional digital CAD model of an anatomic region or of an organ. This alternative way can be provided as a selectable alternative to the one of step 200.

According to this alternative way the three-dimensional digital CAD model relates to a part of the human body comprising more than one anatomic region and/or more than one organ or to the entire human body comprising one or more organs. This digital CAD model is recalled from a memory and loaded in the graphic subunit as indicated at step 208.

At step 209 using selection tools included in the user interface 160 one or more anatomic regions or one or more organs can be selected and used for carrying out the imaging method according to one or more of the embodiments disclosed in the preceding sections.

Figure 3:
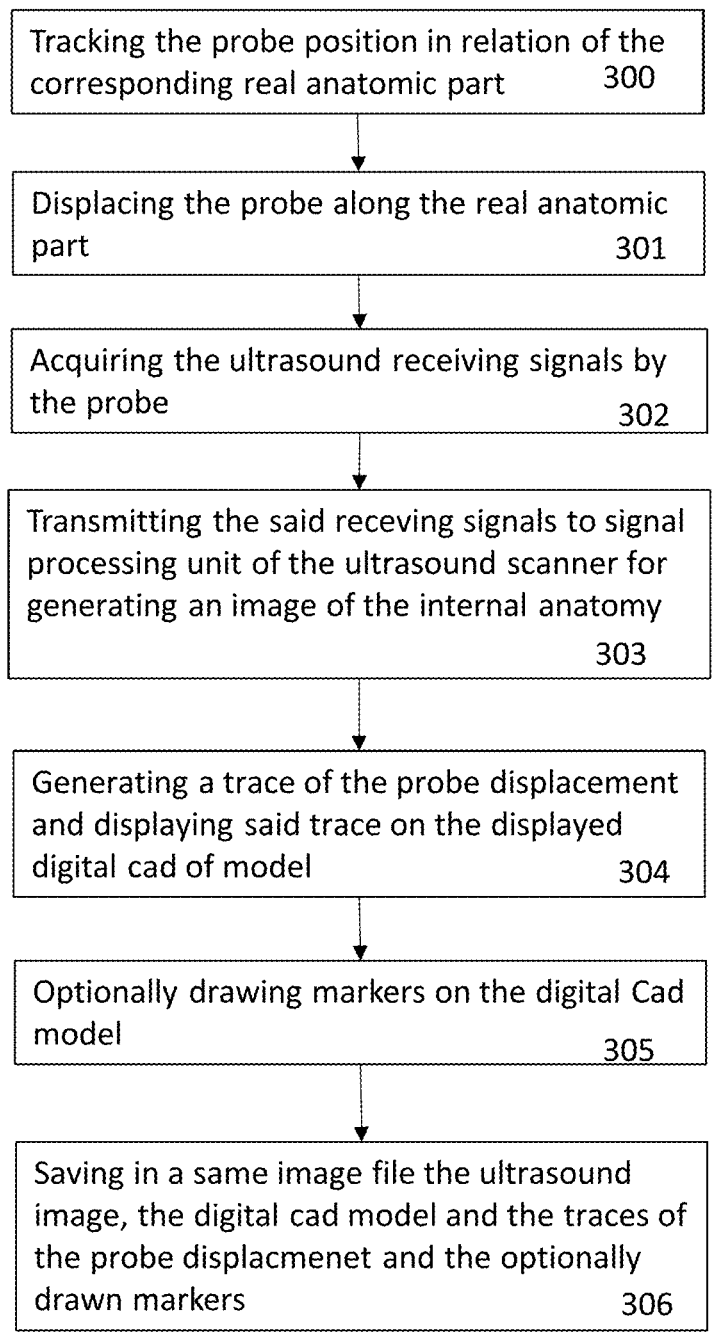

FIG. 3 show the flow chart of the further steps of carrying out the ultrasound imaging scan of the anatomic region or of the organ represented by the three-dimensional digital CAD model matched with the shape of the real anatomic region of the patient as indicated as step 207.

At step 300 the tracking system of the probe is activated and the position, the displacements and the orientation of the probe in a spatial reference system containing the anatomic region to be examined is determined. In order to acquire ultrasound images of an anatomic region several scans have to be carried out along different scan paths, since the probe has a certain aperture and cannot cover the entire extension of the anatomic region to be examined with only one scan passage. Thus the probe is displaced along several scan paths having a certain length from a starting point to an end point, and having a certain width essentially corresponding to the probe aperture. The step is disclosed at step 301.

As indicated at step 302 during each scan, this means during the displacement of the probe along each scan path the ultrasound signals reflected by the tissue are received and processed in order to generate image data from the receipt signals. The acquired receipt signals are sent to a signal processing unit as indicated at step 303 generating the ultrasound image of the tissues scanned along the scan paths.

In order to be able to have a visual indication of the zones of the anatomic region which have been covered by a scan path so that ultrasound images have been acquired for the zones, according to step 304, due to the tracking data of the probe and due to the knowledge about the probe characteristics and particularly about the probe aperture, a trace can be drawn automatically during tracking of the probe. The trace represents the scan paths along a certain zone of the anatomic region or organ represented by the three dimensional digital CAD model and is displayed superimposed on the image representing the model.

According to an embodiment, during scanning it is possible to provide a division of the display in at least two areas which are placed one beside the other. In one of the two display areas the image of the model is displayed, while on the other area the ultrasound image data acquired during each scan can be visualized.

Thus it is possible that during scanning certain interesting objects are discovered such as for example potential lesions. In this case as indicated by step 305, the user can draw or insert a marker point at the trace of the scan paths in the position of the scan trace corresponding essentially to the position at which the object has been discovered.

After having scanned completely or to a certain extent the anatomic region or the organ, an image file is generated as indicated at step 306. This image file corresponds to a combined image comprising the ultrasound image, the digital cad model and the traces of the probe displacement along the scan paths and the optionally drawn markers.

Figure 4:
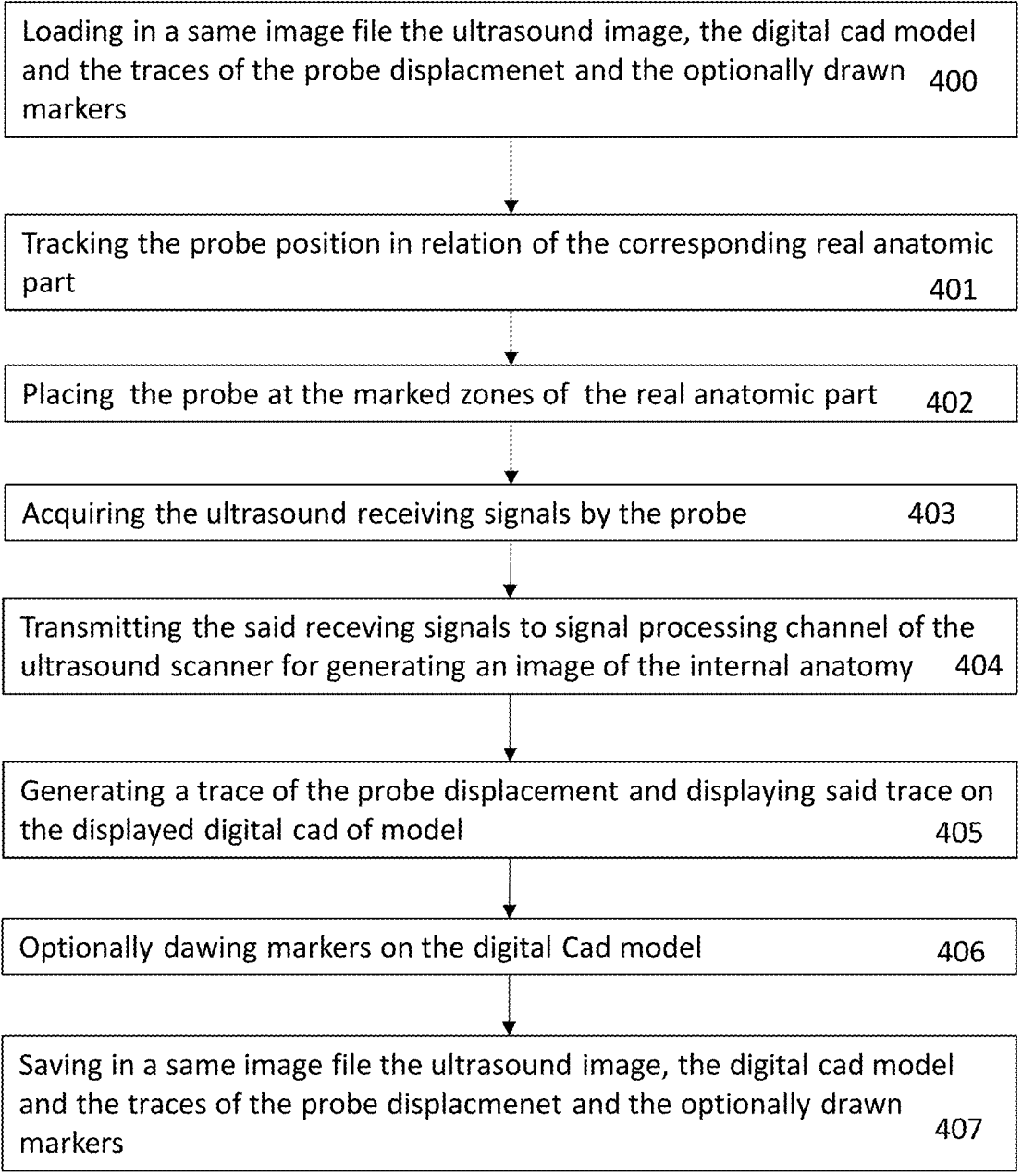

FIG. 4 show a further embodiment of the method according to the present invention which embodiment relates to carrying out further imaging of the same anatomic region or of the same organ at least at one later time with respect to at least one preceding imaging session of the same anatomic region.

When at a later time an ultrasound imaging scan of an anatomic region or of an organ has to be repeated according to the embodiment of FIG. 4 the combined image generated in a previous imaging session and saved at step 306 for a certain patient is loaded as indicated at step 400. The combined image comprises image data formed by the ultrasound image data, the digital cad model and the traces of the probe displacement and the optionally drawn markers of the location of certain object of interest discovered in the ultrasound image data.

The anatomic region of the patient is placed in the tracking reference system of the tracking system of the probe and a new imaging session is started. The tracking system is activated and the probe position, the probe orientation and the probe displacement is tracked as indicated at step 401.

If there is the need of reexamining the evolution of an object of interest discovered in the previous imaging session and if a marker had been placed in the combined image generated in the previous session and saved at step 307, the marker is displayed and placing the probe in a position in relation to the anatomic region such that it coincides with the marker will allow to easily find again the object of interest in the ultrasound image data acquired in this new imaging session as indicated at step 402.

According to an embodiment which is not illustrated in the flow chart of FIG. 4, a reference point registering process may be carried out for registering the real anatomic region under examination with the digital CAD model of the combined image loaded in the graphic subsystem and displayed. The registering process is similar to the one carried out in the first imaging session according to the above disclosed embodiments of the method.

The ultrasound received signals are acquired at step 403 and are processed at step 404 for generating ultrasound image data. Again as indicated by 405 a trace of the probe along the scan paths can be generated and added to the traces of the scan paths already present in the combined image of the previous scan loaded in the graphic subsystem.

Also in this further imaging session markers can be placed as indicated by step 406 and the new combined image can be saved at step 407.

FIG. 5a show the representation of the three dimensional digital CAD model of a breast in a rendering mode before the steps of matching the shape of the real breast of a patient. The reference points are indicated by R1 to R6.

FIG. 5b shows the representation of the three-dimensional digital CAD model of a breast in a rendering mode before the steps of matching the shape of the real breast of a patient. It can be seen clearly by comparing the figures that the shape of the breast represented by the digital CAD model in FIG. 5b has been modified with respect to the shape illustrated in FIG. 5a. In FIG. 5b the position of the reference points at the real breast are indicated as R1' to R6', while the positions of the reference point of FIG. 5a has been indicated with R1 to R6.

FIGS. 9 to 14 show the steps of providing the reference points R1 to R2 on the three-dimensional digital CAD model which is displayed in the raster mode on the screen 901 of an ultrasound scanner 900. The ultrasound scanner has user interfaces 904 and 905 in the form of a key board or similar and in the form of a touch screen. The real breast is simulated by a phantom which is inserted in an opening of a frame of a tracking system 902. The probe 903 is in the position for imaging the reference point R1 on the phantom.

Each one of the FIGS. 9 to 14 show the reference point registering steps for respectively one of the reference points R1 to R6 shown in FIGS. 5a and 5b. Each time the probe 903 is positioned at a different point on the breast phantom corresponding to the position on the breast phantom of one of the reference points on the model displayed on the screen 901.

Figure 16:
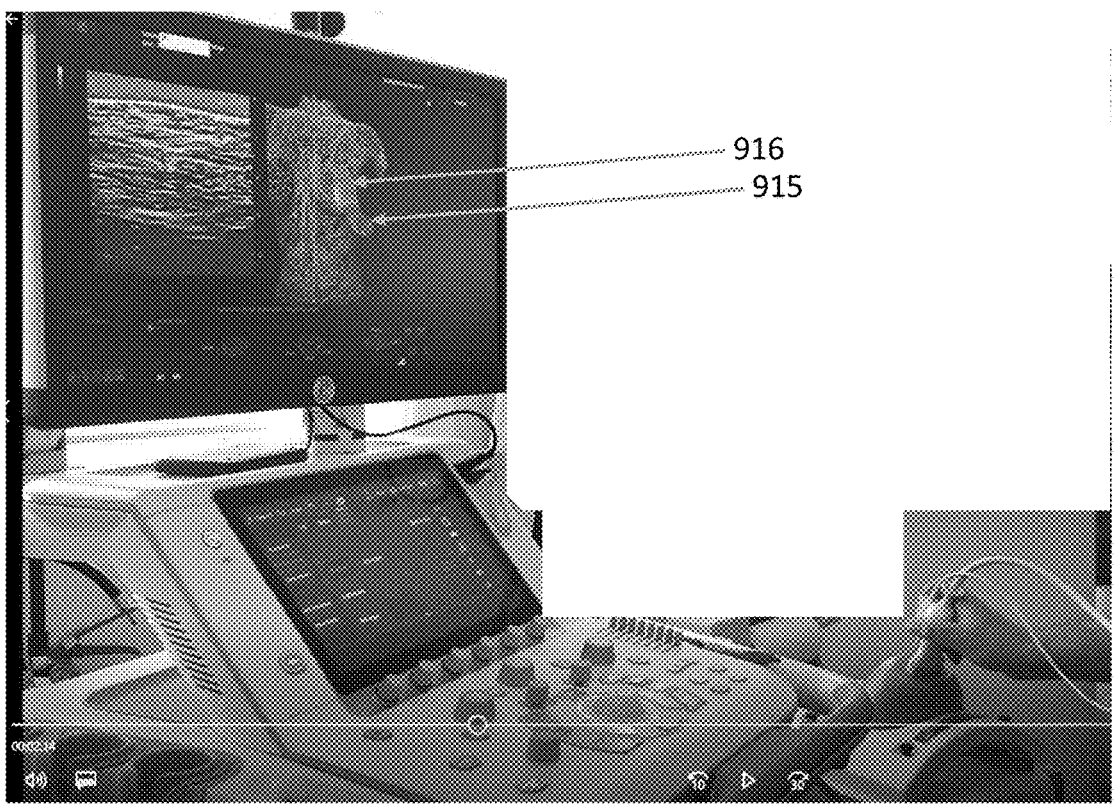

FIGS. 15 to 18 show the process for carrying out the ultrasound imaging scans with an ultrasound imaging apparatus according to the embodiment of the preceding FIGS. 9 to 14. In this case on the screen the image 915 of the probe 903 is represented by also showing the inclination of the probe and thus of the scan plane. The probe 903 is not yet positioned against the surface of the breast phantom. FIG. 16 shows the process of carrying out the first scan displacing the probe 903 along a path on the surface of the breast phantom. On the image of the displayed model, the image of the probe 915 is shown and also the part of the anatomic region which has been scanned by the probe during the displacement on a path, the path is also reproduced and displayed on the image of the model as indicated by 916.

Figure 17:
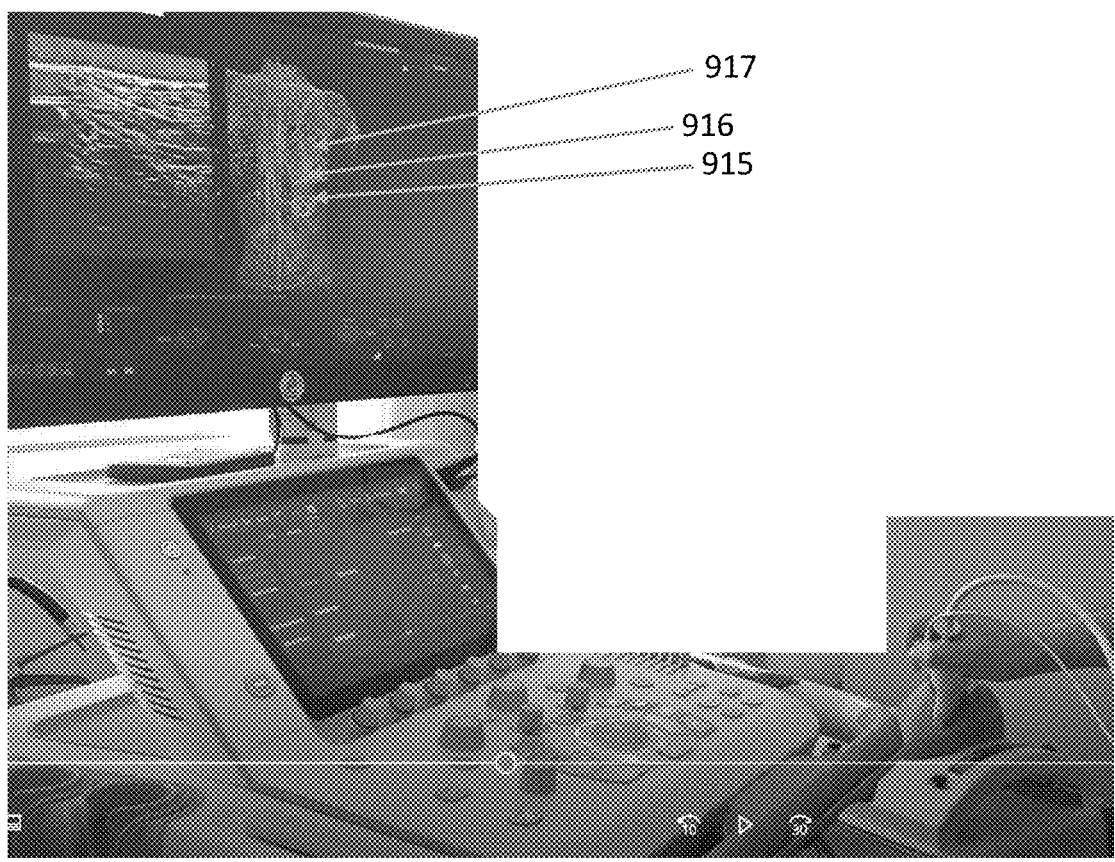

FIG. 17 shows the execution of a further scan according to a scan path which is adjacent to the scan path 916 and is indicated by 917.

Figure 18:
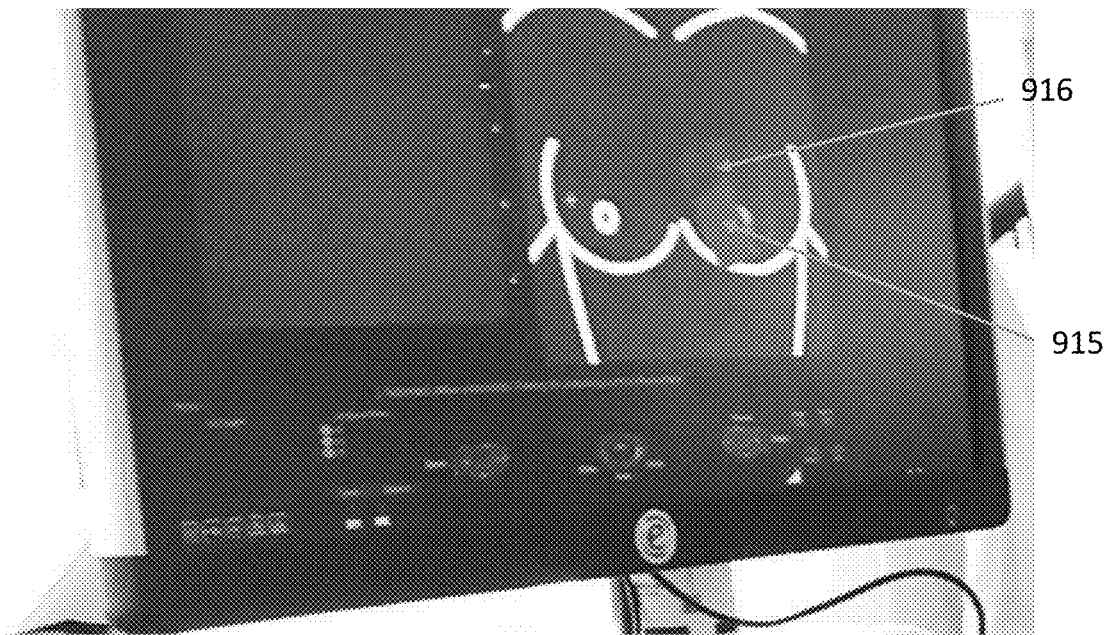

FIG. 18 is a bidimensional projection of the image of the model displayed in the previous FIGS. 16 and 17, In this case the model is simplified but the traces of the scan paths 916 and 917 can be best seen and it is also immediately clear to the user which part of the anatomic region has been examined and which still remain unexamined so that the user can rapidly check if the imaging session is complete or not.

Figure 19:
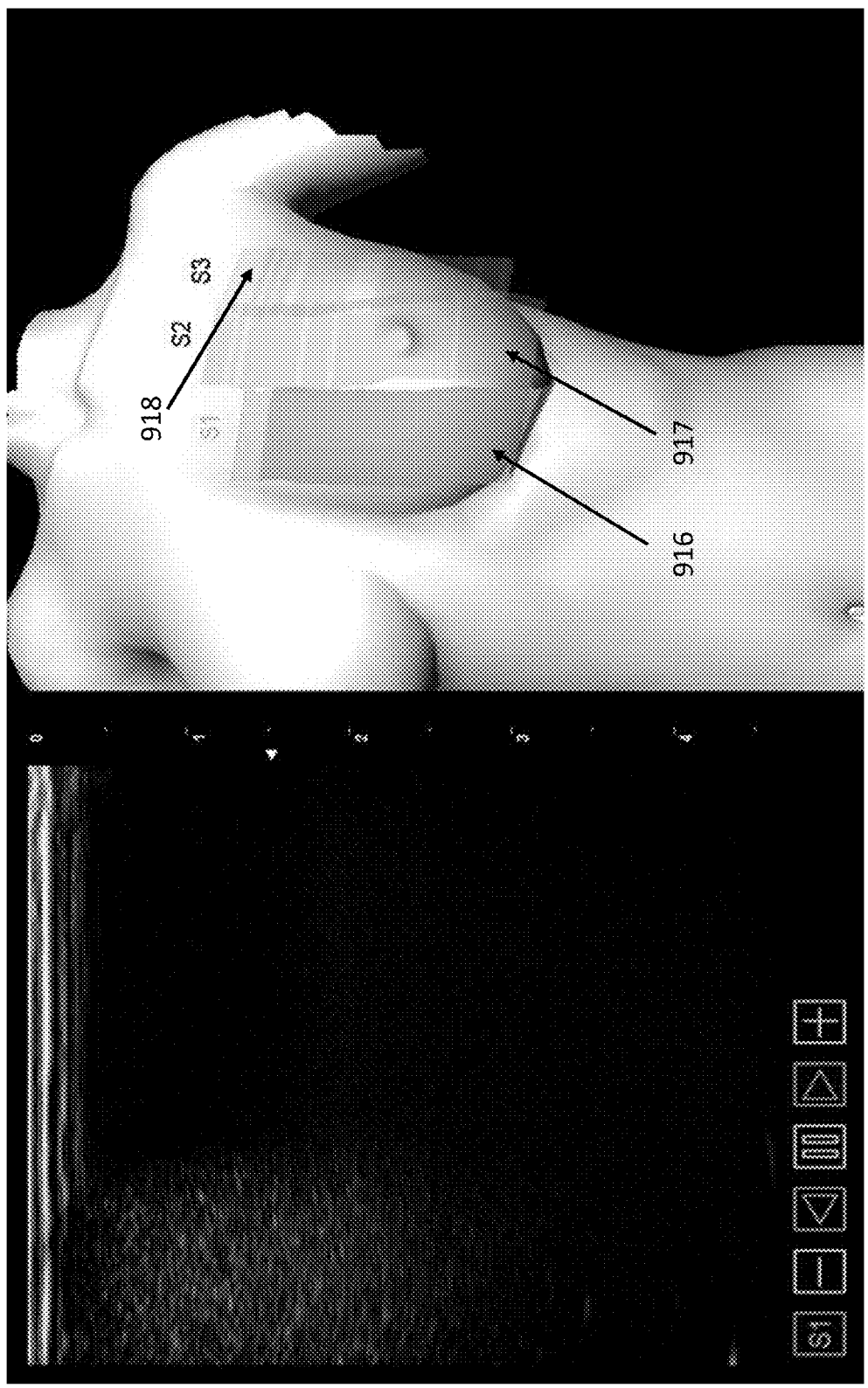

FIG. 19 show in an enlarged view the image of the CAD model displayed and three traces representing the scan paths of the probe indicated by 916, 917 and 918, which traces covers the entire extension of the breast, thereby showing to the user that each part of the region has been scanned and an ultrasound image of the corresponding zone has been generated and saved.

Figure 20:
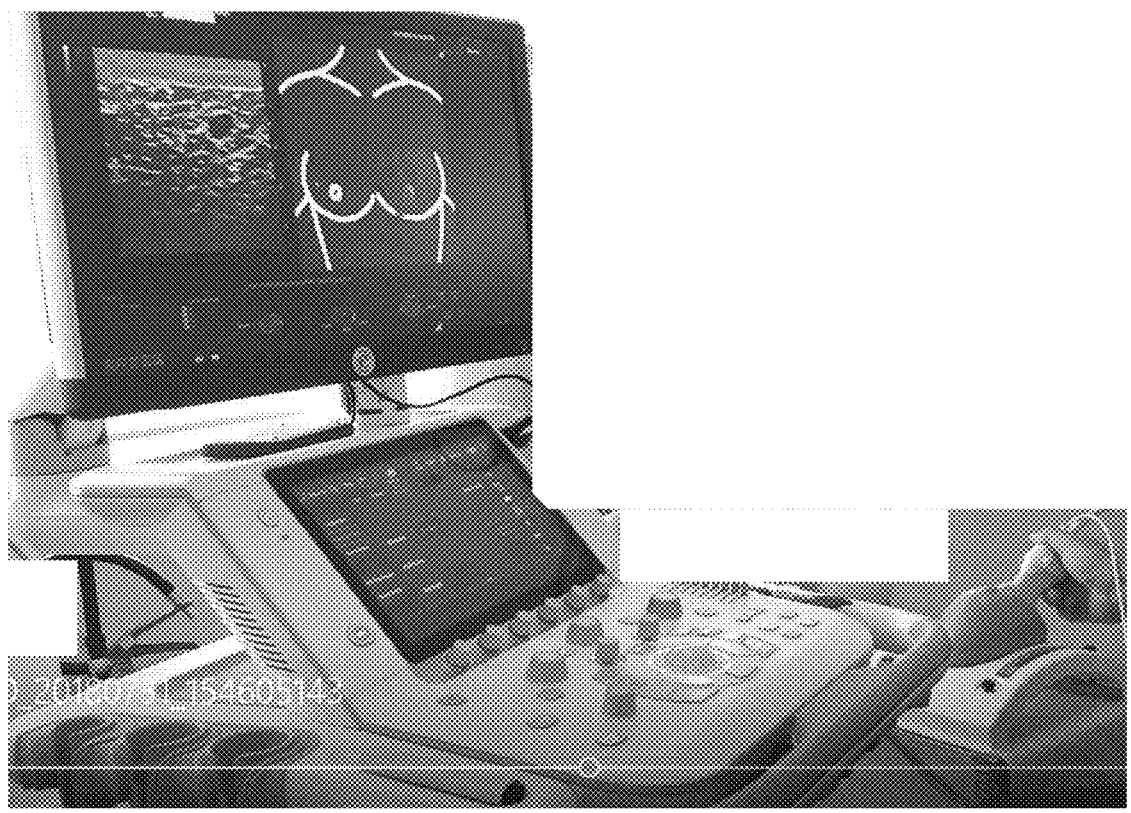

In FIG. 20 a further variant is shown. In this embodiment the ultrasound scanner is the same one as in the previous figures. The process of carrying out scans and showing the traces of the corresponding scan path on the representation of the model is shown to be carried out by using a two-dimensional projection of the three-dimensional model of the breast.

FIG. 21 show that the screen of the display is divided in two adjacent areas 911 and 912. In one area 911 the representation of the model is shown. In the other area 912 the ultrasound image acquires at the marker drawn on the trace 917 of the scan path is shown.

FIG. 22 show a further embodiment of different display modes. In FIG. 22 the screen is divided in four quadrants. Each quadrant displays a different image. One quadrant displays the two dimensional projection of the model, the other quadrants show the ultrasound images according to three different scan plane orientations.

FIGS. 23 and 24 show the steps of carrying an imaging session at a later time of a previous one.

FIG. 23 show the model loaded in the graphic subsystem and printed on screen.

FIG. 24 show the process of placing the probe relatively to the breast phantom in such a way that the image 915 of the probe on the display touches the marker. On the left-hand area of the screen the two ultrasound images of the object of interest at the place of the marker are shown so that a comparison of the evolution of the lesion can be easily made.

FIG. 25 show with an apparatus according to the previous figures, the step of acquiring ultrasound images also at different anatomic regions of a model which encompasses more than one anatomic region. In this case the scan is carried out at the armpit as shown by the image of the probe 915 on the display.

FIG. 6 illustrates a block diagram of an ultrasound system formed in accordance with an alternative embodiment. The system of FIG. 6 implements the operations described herein in connection with various embodiments. By way of example, one or more circuits/processors within the system implement the operations of any processes illustrated in connection with the figures and/or described herein. The system includes a probe interconnect board 602 that includes one or more probe connection ports 704. The connection ports 604 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebro-vascular examination, breast examination and the like.

One or more of the connection ports 604 may support acquisition of 2D image data and/or one or more of the connection ports 604 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 602 includes a switching circuit 606 to select between the connection ports 604. The switching circuit 606 may be manually managed based on user inputs. For example, a user may designate a connection port 604 by selecting a button, switch or other input on the system. Optionally, the user may select a connection port 604 by entering a selection through a user interface on the system.

Optionally, the switching circuit 606 may automatically switch to one of the connection ports 604 in response to detecting a presence of a mating connection of a probe. For example, the switching circuit 606 may receive a "connect" signal indicating that a probe has been connected to a selected one of the connection ports 604. The connect signal may be generated by the probe when power is initially supplied to the probe when coupled to the connection port 604. Additionally, or alternatively, each connection port 604 may include a sensor 605 that detects when a mating connection on a cable of a probe has been interconnected with the corresponding connection port 604. The sensor 605 provides signal to the switching circuit 606, and in response thereto, the switching circuit 606 couples the corresponding connection port 604 to PIB outputs 608. Optionally, the sensor 605 may be constructed as a circuit with contacts provided at the connection ports 604. The circuit remains open when no mating connected is joined to the corresponding connection port 604. The circuit is closed when the mating connector of a probe is joined to the connection port 604.

A control line 624 conveys control signals between the probe interconnection board 602 and a digital processing board 624. A power supply line 636 provides power from a power supply 640 to the various components of the system, including but not limited to, the probe interconnection board (PIB) 602, digital front end boards (DFB) 610, digital processing board (DPB) 626, the master processing board (M PB) 644, and a user interface control board (UI CB) 646.

A temporary control bus 638 interconnects, and provides temporary control signals between, the power supply 640 and the boards 602, 610, 626, 644 and 646. The power supply 640 includes a cable to be coupled to an external AC power supply. Optionally, the power supply 640 may include one or more power storage devices (e.g. batteries) that provide power when the AC power supply is interrupted or disconnected. The power supply 640 includes a controller 642 that manages operation of the power supply 640 including operation of the storage devices.

Additionally, or alternatively, the power supply 640 may include alternative power sources, such as solar panels and the like. One or more fans 643 are coupled to the power supply 640 and are managed by the controller 642 to be turned on and off based on operating parameters (e.g. temperature) of the various circuit boards and electronic components within the overall system (e.g. to prevent overheating of the various electronics).

The digital front end boards 610 include transmit driver circuits 612 that generate transmit signals that are passed over corresponding channels to the corresponding transducers in connection with ultrasound transmit firing operations. The transmit driver circuits 612 provide pulse or control for each drive signal and transmit beamforming management to steer firing operations to points of interest within the region of interest. By way of example, a separate transmit driver circuits 612 may be provided in connection with each individual channel, or a common transmit driver circuits 612 may be utilized to drive multiple channels. The transmit driver circuits 612 cooperate to focus transmit beams to one or more select points within the region of interest. The transmit driver circuits 612 may implement single line transmit, encoded firing sequences, multiline transmitter operations, generation of shear wave inducing ultrasound beams as well as other forms of ultrasound transmission techniques.

The digital front end boards 610 include receive beamformer circuits 614 that received echo/receive signals and perform various analog and digital processing thereon, as well as phase shifting, time delaying and other operations in connection with beamforming. The beam former circuits 614 may implement various types of beamforming, such as single-line acquisition, multiline acquisition as well as other ultrasound beamforming techniques.

The digital front end boards 616 include continuous wave Doppler processing circuits 616 configured to perform continuous wave Doppler processing upon received echo signals. Optionally, the continuous wave Doppler circuits 616 may also generate continuous wave Doppler transmit signals.

The digital front-end boards 610 are coupled to the digital processing board 626 through various buses and control lines, such as control lines 622, synchronization lines 620 and one or more data bus 618. The control lines 622 and synchronization lines 620 provide control information and data, as well as synchronization signals, to the transmit drive circuits 612, receive beamforming circuits 614 and continuous wave Doppler circuits 616. The data bus 618 conveys RF ultrasound data from the digital front-end boards 610 to the digital processing board 626. Optionally, the digital front end boards 610 may convert the RF ultrasound data to I,Q data pairs which are then passed to the digital processing board 626.

The digital processing board 626 includes an RF and imaging module 628, a color flow processing module 630, an RF processing and Doppler module 632 and a PCI link module 634. The digital processing board 626 performs RF filtering and processing, processing of black and white image information, processing in connection with color flow, Doppler mode processing (e.g. in connection with polls wise and continuous wave Doppler). The digital processing board 626 also provides image filtering (e.g. speckle reduction) and scanner timing control. The digital processing board 626 may include other modules based upon the ultrasound image processing functionality afforded by the system.

The modules 628-634 comprise one or more processors, DSPs, and/or FPGAs, and memory storing program instructions to direct the processors, DSPs, and/or FPGAs to perform various ultrasound image processing operations. The RF and imaging module 628 performs various ultrasound related imaging, such as B mode related image processing of the RF data. The RF processing and Doppler module 632 convert incoming RF data to I,Q data pairs, and performs Doppler related processing on the I, Q data pairs. Optionally, the imaging module 628 may perform B mode related image processing upon I, Q data pairs. The CFM processing module 630 performs color flow related image processing upon the ultrasound RF data and/or the I, Q data pairs. The PCI link 634 manages transfer of ultrasound data, control data and other information, over a PCI express bus 648, between the digital processing board 626 and the master processing board 644.

The modules 628-634 comprise one or more processors, DSPs, and/or FPGAs, and memory storing program instructions to direct the processors, DSPs, and/or FPGAs to perform various ultrasound image processing operations. The RF and imaging module 628 performs various ultrasound related imaging, such as B mode related image processing of the RF data. The RF processing and Doppler module 632 convert incoming RF data to I,Q data pairs, and performs Doppler related processing on the I, Q data pairs. Optionally, the imaging module 628 may perform B mode related image processing upon I, Q data pairs. The CFM processing module 730 performs color flow related image processing upon the ultrasound RF data and/or the I, Q data pairs. The PCI link 634 manages transfer of ultrasound data, control data and other information, over a PCI express bus 648, between the digital processing board 626 and the master processing board 644.

The network devices 666 may represent portable or desktop devices, such as smart phones, personal digital assistants, tablet devices, laptop computers, desktop computers, smart watches, ECG monitors, patient monitors, and the like. The master processing board 644 conveys ultrasound images, ultrasound data, patient data and other information and content to the network devices for presentation to the user. The master processing board 644 receives, from the network devices 666, inputs, requests, data entry and the like.

The network server 668 may represent part of a medical network, such as a hospital, a healthcare network, a third-party healthcare service provider, a medical equipment maintenance service, a medical equipment manufacturer, a government healthcare service and the like. The communications link to the network server 668 may be over the Internet, a private intranet, a local area network, a wide-area network, and the like.

The master processing board 644 is connected, via a communications link 670 with a user interface control board 646. The communications link 670 conveys data and information between the user interface and the master processing board 644. The user interface control board 646 includes one or more processors 672, one or more audio/video components 674 (e.g. speakers, a display, etc.). The user interface control board 646 is coupled to one or more user interface input/output devices, such as an LCD touch panel 676, a trackball 678, a keyboard 680 and the like. The processor 672 manages operation of the LCD touch panel 676, as well as collecting user inputs via the touch panel 676, trackball 678 and keyboard 680, where such user inputs are conveyed to the master processing board 644 in connection with implementing embodiments herein.

In relation to this embodiment of an ultrasound system, it has to be noted that although the channels or the feeding lines of the transducer elements of the array of the probe are not provided with a switch opening and closing the line, the functions of this switches can be carried out not by hardware such as the switches but by one or more of the processing units provided in the transmit beam generation section which are configured by a program to carry out the functions of the switches. The program comprising the instructions to configure the processing units as switches operating according to the method of the present invention as described in the previous embodiments.

FIG. 7 illustrates a block diagram of a portion of the digital front-end boards 610 formed in accordance with embodiments herein. A group of diplexers 702 receive the ultrasound signals for the individual channels over the PIB output 708. The ultrasound signals are passed along a standard processing circuit 705 or to a continuous wave processing circuit 712, based upon the type of probing utilized. When processed by the standard processing circuit 705, a preamplifier and variable gain amplifier 704 process the incoming ultrasound receive signals that are then provided to an anti-aliasing filter 706 which performs anti-aliasing filtering.

According to an embodiment the retrospective transmit beam focusing according to the present invention may be applied to the RF data directly acquired by the system or to transformed data according to different transformations as for example as a phase/quadrature (I/Q) transformation, or similar.

In the embodiment of FIG. 7 an example of the transformation of the RF data is disclosed. According to this example, the output of the filter 706 is provided to an A/D converter 708 that digitizes the incoming analog ultrasound receive signals. When a continuous wave (CW) probe is utilized, the signals therefrom are provided to a continuous wave phase shifter, demodulator and summer 710 which converts the analog RF receive signals to I,Q data pairs. The CW I,Q data pairs are summed, filtered and digitized by a continuous wave processing circuit 712. Outputs from the standard or continuous wave processing circuits 705, 712 are then passed to beam forming circuits 820 which utilize one or more FPGAs to perform filtering, delaying and summing the incoming digitized receive signals before passing the RF data to the digital processing board 726 (FIG. 6). The FPGAs receive focalization data from memories 728. The focalization data is utilized to manage the filters, delays and summing operations performed by the FPGAs in connection with beamforming. The beamformed RF or I/Q data is passed between the beamforming circuits 720 and ultimately to the digital processing board 626.

The digital front-end boards 610 also include transmit modules 722 that provide transmit drive signals to corresponding transducers of the ultrasound probe. The beamforming circuits 720 include memory that stores transmit waveforms. The transmit modules 722 receive transmit waveforms over line 724 from the beamforming circuits 720.

FIG. 8 illustrates a block diagram of the digital processing board 626 implemented in accordance with embodiments herein. The digital processing board 626 includes various processors 852-859 to perform different operations under the control of program instructions saved within corresponding memories see 862-869. A master controller 950 manages operation of the digital processing board 626 and the processors 852-859. By way of example, one or more processors as the 852 may perform filtering, the modulation, compression and other operations, while another processor 853 performs color flow processing. The master controller provides probe control signals, timing control signals, communications control and the like. The master controller 850 provides real-time configuration information and synchronization signals in connection with each channel to the digital front-end board 610.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGP") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database serve The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

The references, including publications, patent applications and patents, cited herein are hereby incorporated by reference to the same extent as if each reference were individually and specifically indicated to be incorporated by reference and were set forth in its entirety herein.

The invention claimed is:

1. An ultrasound imaging method comprising:
providing a digital representation of a shape of a surface or a boundary of an anatomic region or of an organ;
acquiring an ultrasound image by ultrasound scanning the anatomic region or the organ;
combining a digital representation of the shape of the surface or the boundary of the anatomic region or of the organ by:
registering the digital representation of the shape of the surface or the boundary and the ultrasound image as a function of a difference in position of selected reference points on the digital representation of the shape or the boundary and on the ultrasound image, a position of the reference points on the ultrasound image being determined by tracking probe position at the reference points at the anatomic region or the organ of a real body and in a spatial reference system, in which the anatomic region or the organ of the real body is placed, wherein:
the digital representation is a three dimensional digital CAD model of the anatomic region or of the organ on which the reference points are defined;
the digital representation is morphologically non-patient specific;
the shape of the surface or of the boundary of the digital CAD model is modified to match the shape of the surface or of the boundary of a real anatomic region or the shape of a real organ specific for a patient, as a function of a difference in position of the reference points in the digital CAD model and the position of the same reference points on the real anatomic region or on the real organ specific for the patient,
the position of the reference points on the anatomic region or the organ of the real body is determined by tracking the probe position at the reference points at the anatomic region or the organ of the real body and in the spatial reference system, in which the anatomic region or the organ of the real body is placed,
the ultrasound scanning of the anatomic region or the organ of the real body to acquire the ultrasound image of the anatomic region or of the organ is executed by moving a probe according to one or more scan paths along at least part of the surface of the anatomic region or of the organ, each of the one or more scan paths having a length, a width, and a shape;
tracking the probe position during a displacement of the probe along the one or more scan paths for determining data providing a digital representation of the one or more scan paths of the probe relative to the length, the width, and the shape of the one or more scan paths and to a position of the one or more scan paths in relation to the anatomic region or the organ of the real body being scanned;
registering the data relative to the position of the one or more scan paths, the length, the width, and the shape of the one or more scan paths with the digital CAD model which has been matched with the shape of the real anatomic region or of a real boundary;
graphically representing the one or more scan paths on the digital CAD model of the anatomic region or of the organ matched to a real shape of the anatomic region or the organ of the patient under examination to develop a three-dimensional digital representation of the anatomic region or the organ of the real body and of the one or more scan paths of the ultrasound probe along which the probe has been displaced during the ultrasound scanning of the anatomic region or the organ of the real body, the three-dimensional digital representation of the one or more scan paths being superimposed on the three-dimensional digital representation of the anatomic region or the organ of the real body;
combining and saving the three-dimensional digital representation and the acquired ultrasound image; and
displaying and/or printing a combination of three-dimensional digital representation and the acquired ultrasound image.

2. The ultrasound imaging method according to claim 1, wherein the three dimensional digital CAD model comprises different anatomic regions of a body and encompasses different organs, which are inside the anatomic region,
further comprising the step of selecting a part of the different anatomical regions or of the different organs to be used in carrying out the steps of the method.

3. The ultrasound imaging method according to claim 1, wherein the three dimensional digital CAD model represents entire anatomic regions of the real body and entire organs in the real body,
further comprising the step of selecting one or more of the anatomical regions or of the organs represented in the digital CAD model to be used in carrying out the steps of the method.

4. The ultrasound imaging method according to claim 1, wherein tracking of the probe position and movements in the reference system comprises tracking probe orientation or tracking an orientation of a scan plane generated by the probe and generating a graphic representation of the shape of the probe and of an orientation of the probe in relation to a three-dimensional digital CAD model of the surface or of the boundary of the anatomic region or of the organ, the graphic representation of the probe being displayed in combination with the three-dimensional digital CAD model oriented and displaced along a scan path according to an orientation and displacement of the probe along the scan path on the surface of the anatomic region or the organ.

5. The ultrasound imaging method according to claim 1, further comprising the step of drawing or inserting markers in a matched three dimensional digital CAD model, the markers being graphically distinguished from a digital CAD representation of the anatomic region or of the organ, a graphic representation of the markers and/or a position on the digital CAD model being combined with a graphic representation of a three-dimensional digital CAD model, the markers being displayed together with the representation of the digital CAD model, the markers are saved on a combined image of the ultrasound image and of the three-dimensional digital CAD model matched to the real shape of the anatomic region or of the organ of the body of the patient.

6. The ultrasound imaging method according to claim 5, wherein a display screen is divided in regions that display, at a same time and in different regions of a display, one beside the other, different views, and in wherein, in at least one display area, there is shown the combined image of the anatomic region as modified by matching to the real anatomic region of the patient and of tracking of the probe and, or of the inserted marker or markers when inserted.

7. The ultrasound imaging method according to claim 6, wherein the digital CAD model of the anatomic region or of the organ is displayed as a three-dimensional image or as a two dimensional projection image of the three-dimensional digital CAD model on a two dimensional plane having a predefine orientation in relation to the three-dimensional digital CAD model.

8. The ultrasound imaging method according to claim 6, wherein, in at least one additional area of the display regions, there is displayed the ultrasound image along one selected scan plane intersecting or passing through a position identified by at least one of the markers or having a predetermined position and orientation relatively to the at least one of the markers.

9. The ultrasound imaging method according to claim 6, further comprising a display region in the display, in which the ultrasound image along an additional selected scan plane intersects or passes through the position identified by at least one of the markers or having a predetermined position and orientation relative to the at least one of the markers, wherein the position and/or the orientation is different from other scan planes, along which the ultrasound images are shown in at least one display region.

10. The ultrasound imaging method according to claim 5, further comprising additional steps of carrying out a second ultrasound imaging scan of the patient and of the anatomic region or of the organ following an initial ultrasound imaging scan, the additional steps comprising:
retrieving an image of a three-dimensional digital CAD model of the anatomic region combined with the images of the scan path already carried out and with the ultrasound images acquired along scan planes and with at least one marker when inserted, to generate combined images;
displaying, superimposed to the combined images, a set of the selected reference points;
registering the shape of the surface of the anatomic region and or of the organ with a shape of a three dimensional representation of the anatomic region or the organ by one of the combined images as a function of differences in a position of one or more of the reference points on the one of the combined images and the position of points determined by tracking the probe position at the reference points provided on the surface of the anatomic region or the organ of the real body of the patient;
tracking the probe position and orientation in a reference system, in which the anatomic region or the organ is placed and positioning the probe at one or more of the markers for generating ultrasound image data of a same object as in a previous ultrasound image scan and along at least one identical scan plane having one identical orientation relative to the scan plane of the previous ultrasound imaging scan;
comparing images obtained in the previous ultrasound imaging scan at a same marker point with the image obtained in a second following ultrasound imaging scan; and
displaying the ultrasound image.

11. An ultrasound imaging system configured to carry out a method according to claim 1, the ultrasound imaging system comprising:
a probe comprising electro-acoustic transducers grouped as one array of transducers, the electro-acoustic transducers generating ultrasound signals upon excitation by an electric driving signal and generating electric signals upon receipt of reflected ultrasound signals;
an ultrasound signal processing unit configured to receive the electric signals generated by the reflected ultrasound signals falling on the electro-acoustic transducers and to process the electro-acoustic signals to generate image data related to a target body, in which reflectors of a transmitted ultrasound signals are provided;
a probe tracking system configured to determine a position of the probe in a space defined by a spatial reference system and to further determine an orientation of a scan plane generated by the probe;
a memory, in which a three-dimensional digital CAD model of at least one anatomic region or of at least one organ is stored, and from which the digital CAD model can be retrieved and loaded in a processor;
the processor being configured to process image data of the three-dimensional digital CAD model and ultrasound image data generated by the ultrasound signal processing unit;
the processor being further configured to receive the position of the probe and orientation data and to generate a virtual model of the probe and graphic representations of traces of a path of the probe along one or more specific scan paths;
an input interface configured to define a position of one or more reference points in relation to a shape of the surface of the anatomic region or the organ represented by the digital CAD model; and
the processor being configured to process the difference in the position of the probe at the position of the reference points on the surface of the anatomic region of the organ of the real body and to modify the shape of the surfaces of the anatomic region or the organ of the three-dimensional digital CAD model as a function of the difference in position of the reference points positioned on the three-dimensional digital CAD model and on the real anatomic region or the real organ;
the processor being further configured to register a modified three-dimensional digital CAD model with the representation of traces of the one or more specific scan paths of the probe along the surface of the anatomic region or of the organ and the ultrasound images generated from each specific scan path, and to combine image data in a combined image;
the processor being further configured to track the probe position during a displacement of the probe along the one or more specific scan paths and to determine data providing a digital representation of the one or more specific scan paths of the probe relative to lengths, widths, and shapes of the one or more specific scan paths and to positions of the one or more specific scan paths in relation to the at least one anatomic region or the at least one organ being scanned;
the processor being further configured to register the data relative to the position of the one or more scan paths, the length, the width, and the shape of the one or more scan paths with the digital CAD model which has been matched with the shape of the real anatomic region or of a real boundary;
the processor being further configured to match the one or more scan paths on the digital CAD model of the anatomic region or of the organ with a real shape of the anatomic region or the organ of the patient under examination, to develop a three-dimensional digital representation of the anatomic region or the organ of the real body and of the one or more scan paths path of the ultrasound probe along which the probe has been displaced during the ultrasound scanning of the anatomic region or the organ of the real body, and to superimpose the three-dimensional digital representation of the one or more scan paths on the three-dimensional digital representation of the anatomic region or the organ of the real body; and a display configured to receive an output of the processor and to display the combined image data processed by the processor.

12. The ultrasound imaging system according to claim 11, further comprising:

a memory, in which three-dimensional digital CAD models of different anatomic regions of a body and/or of different organs are stored, the digital CAD models being retrieved and loaded in the processor to be processed; and a user interface including a selector for selecting the digital CAD models of at least one anatomic region or organ and for loading the selected model in the processor.

13. The ultrasound imaging system according to claim 11, further comprising:

a memory, in which a three-dimensional digital CAD model of a complete body is stored, and a user interface including a selector for selecting parts of the digital CAD model of the complete body representing at least one anatomic region or at least one organ and for loading the selected parts of the digital CAD model in the processor.

14. The ultrasound imaging system according to claim 11, further comprising an input device that draws or sets markers at a specific position on the three-dimensional digital CAD model of the at least one anatomic region or the at least one organ.

15. The ultrasound imaging system according to claim 14, further comprising:

a memory that stores a combined image comprising the three-dimensional digital CAD model of the at least one anatomic region or the at least one organ, modified for matching a real shape of a real anatomic region of the real body of a patient, and in combination therewith ultrasound image data of the anatomic region or of the organ, traces of scan paths of the probe along the surface of the anatomic region or the organ registered with the shape of the anatomic region or of the organ represented by the model, and the markers, when present, set by a user for distinguishing and highlighting positions of relevant structures or features in the ultrasound images;

a user interface that addresses the memory and retrieves the combined image and displays on the display; and an input device that sets, on the combined image, reference points for carrying out a registration of the real shape of the surface of the real anatomic region of the body of a patient or of a real organ with the shape represented in a combined region.

16. The ultrasound imaging system according to claim 14, further comprising:

a memory that saves a sequence of combined image each comprising the three-dimensional digital CAD model of the at least one anatomic region or the at least one organ after having been modified for matching a real shape of a real anatomic region of the body of the patient, and in combination therewith ultrasound image data of the anatomic region or of the organ, traces of the one or more scan paths along the surface of the anatomic region or the organ registered with the shape of the anatomic region or of the organ represented by the digital CAD model, and of the markers, when present, markers set by a user for distinguishing and highlighting positions of relevant structures or features in the ultrasound images acquired or set at different times.

* * * * *